US011208371B2

(12) United States Patent
Henderson

(10) Patent No.: US 11,208,371 B2
(45) Date of Patent: Dec. 28, 2021

(54) COMPOUNDS, COMPOSITIONS, AND METHODS FOR USE IN TREATING AUTOPHAGY-ASSOCIATED DISORDERS

(71) Applicant: Biophagy, Inc., Albuquerque, NM (US)

(72) Inventor: Ian Henderson, Albuquerque, NM (US)

( * ) Notice: Subject to any disclaimer, the term of this patent is extended or adjusted under 35 U.S.C. 154(b) by 0 days.

(21) Appl. No.: 16/717,728

(22) Filed: Dec. 17, 2019

(65) Prior Publication Data
US 2020/0190007 A1 Jun. 18, 2020

Related U.S. Application Data

(60) Provisional application No. 62/780,615, filed on Dec. 17, 2018.

(51) Int. Cl.
| | |
|---|---|
| *C07C 49/225* | (2006.01) |
| *C07C 49/255* | (2006.01) |
| *C07C 235/64* | (2006.01) |
| *C07D 213/30* | (2006.01) |
| *C07D 263/56* | (2006.01) |
| *C07D 498/04* | (2006.01) |
| *A61K 45/06* | (2006.01) |
| *A61K 31/44* | (2006.01) |
| *A61K 31/167* | (2006.01) |
| *A61K 31/536* | (2006.01) |
| *A61K 31/5365* | (2006.01) |
| *A61K 31/12* | (2006.01) |

(52) U.S. Cl.
CPC ............ *C07C 49/255* (2013.01); *A61K 31/12* (2013.01); *A61K 31/167* (2013.01); *A61K 31/44* (2013.01); *A61K 31/536* (2013.01); *A61K 31/5365* (2013.01); *A61K 45/06* (2013.01); *C07C 235/64* (2013.01); *C07D 213/30* (2013.01); *C07D 263/56* (2013.01); *C07D 498/04* (2013.01)

(58) Field of Classification Search
CPC .................................... C07C 49/255
USPC ......................................... 546/90
See application file for complete search history.

(56) References Cited

U.S. PATENT DOCUMENTS

| | | | |
|---|---|---|---|
| 6,004,719 A | 12/1999 | Gaudiana et al. | |
| 2014/0135296 A1* | 5/2014 | Deretic | A61K 31/519 514/154 |

OTHER PUBLICATIONS

Karki European Journal of Medicinal Chemistry (2014), 84, 555-565.*
Hagel, Frontiers in Plant Physiology, 2010, 1(14), 1-7.*
Olah, PNAS, 2011, 108(15), 6050-6055.*
Smith, JCS Perkin II, 1983, 621-628.*

Zhang et al. "Intestinal and Hepatic Glucuronidation of Flavonoids". Molecular Pharmaceutics. vol. 4, No. 6, pp. 833-845. Published Sep. 13, 2007.
Saleh et al. "Antagonism Between Curcumin and the Topoisomerase II Inhibitor Etoposide". Landes Bioscience. Published Aug. 16, 2012.
Karki et al. "Synthesis, antitumor activity, and structure-activity relationship study of trihydroxylated 2,4,6-triphenyl pyridines as potent selective topoisomerase II inhibitors". European Journal of Medicinal Chemistry. 2014.
Bist et al. "Dihydroxylated 2,6 diphenyl-4-chlorophenylpyridines: Topoisomerase I and II-alpha dual inhibitors with DNA non-intercalative catalytic activity." European Journal of Medicinal Chemistry. 2017.
PubChem—CID—132519893. Compound Summary. 2018.
PCT/US2019/66934. "International Search Report and Written Opinion" dated Dec. 17, 2019.
Rohokale et al. "Synthesis of 2,4,6-Trisubstituted Pyridines by Oxidative Eosin Y Photoredox Catalysis." Journal of Organic Chemistry. 7121-7126 (2016).
Hagel et al. "Briochemistry and Occurrence of O-Demethylation in Plant Metabolism." Frontiers in Plant Physiology. Article 14, p. 1-7 (2010).
PCT/US2019/66934. "International Preliminary Report on Patentability" dated Feb. 10, 2021. 41 pages.
Yun et al. The Roles of Autophagy in Cancer. International Journal of Molecular Sciences. Nov. 2018.
*Amerigen Pharmaceuticals Limited v. UCB Pharma GMBH.* 2017-2596. Appeal from the United States Patent and Trademark Office, Patent Trial and Appeal Board in No. IPR2016-01665. Decided: Jan. 11, 2019.
Bartlett et al. Autophagic dysregulation in doxorubicin cardiomyopathy. Journal of Molecular and Cellular Cardiology. Jan. 2017.
Brel et al. Cytotoxicity and cell death mechanisms induced by the polyamine-vectorized anti-cancer drug F14512 targeting topoisomerase II. Biochemical Pharmacology. Sep. 2011.
*Daiichi Sankyo Company, Ltd and Daiichi Sankyo, Inc. v. Matrix Laboratories, Ltd., Mylan Inc., Mylan Laboratories, Inc., and Mylan Pharmaceuticals, Inc.* 2009-1511. Appeal from the United States District Court for the District of New Jersey in Case No. 06-CV-03462, Judge William J. Martini. Decided: Sep. 9, 2010.
*Otsuka Pharmaceutical Co., Ltd. v. Sandoz, Inc., Sun Pharmaceutical Industries, Ltd., Synthon BV, Synthon Holdings BV, Synthon Laboratories, Inc., and Sython Pharmaceuticals, Inc. and Apotex Inc. and Apotex Corp. and Teva Pharmaceuticals USA, Inc., Barr Laboratories Inc., and Barr Pharmaceuticals, Inc.* 2011-1126, -1127. Appeal from the United States District Court for the District of New Jersey in Case No. 07-CV-1000, Judge Mary L. Cooper. Decided: May 7, 2012.

(Continued)

*Primary Examiner* — Nizal S Chandrakumar
(74) *Attorney, Agent, or Firm* — Katherine M. Bond; Katherine B. Sales; Cislo & Thomas LLP

(57) ABSTRACT

The invention provides compounds and methods of treating autophagy mediated diseases and disorders and related pharmaceutical compositions, diagnostics, screening techniques and kits.

32 Claims, No Drawings

(56) References Cited

OTHER PUBLICATIONS

Saleh et al. Antagonism between curcumin and the topoisomerase II inhibitor etoposide: A study of DNA damage, cell cycle regulation and death pathways. Cancer Biology & Therapy. Aug. 2012.
*Takeda Chemical Industries, Ltd. and Takeda Pharmaceuticals North America, Inc.* v. *Alphapharm Pty., Ltd. and Genpharm, Inc.* United States Court of Appeals for the Federal Circuit. 06-1329. Decided: Jun. 28, 2007.

\* cited by examiner

COMPOUNDS, COMPOSITIONS, AND METHODS FOR USE IN TREATING AUTOPHAGY-ASSOCIATED DISORDERS

CROSS-REFERENCE TO RELATED APPLICATIONS

This application claims priority to U.S. Provisional Application No. 62/780,615, titled "Compositions and Methods for use in Treating Autophagy-Associated Disorders," filed Dec. 17, 2018, the contents of which are incorporated by reference in their entirety.

FIELD OF THE INVENTION

The invention provides compounds, compositions, and methods for treating autophagy-associated disorders and related pharmaceutical compositions, diagnostics, screening techniques and kits.

BACKGROUND

Autophagy is a homeostatic process that is highly conserved in eukaryotic cells, where it acts as a cytoplasmic biomass quantity and quality control system (Mizushima N., et al., Nature (2008) 451, 1069-1075; Yang Z., and Klionsky, D. J., Nat. Cell Biol. (2010) 12, 814-822). Autophagy functions encompass programmed cell survival and cell death, normally skewed toward cell survival (Kroemer G. and Levine, B., Nat Rev Mol Cell Biol (2008) 9, 1004-1010) through provision of energy and nutrients and ridding the cytoplasm of toxic macromolecular aggregates, faulty organelles (Mizushima, et al., 2008; Yang Z., and Klionsky, D. J., 2010) and invading microorganisms (Deretic, V., and Levine, B., Cell Host Microbe (2009) 5, 527-549; Levine, B., et al., Nature (2011) 469, 323-335).

The cell-autonomous antimicrobial defense functions of autophagy, demonstrated initially in the case of *Streptococci* (Nakagawa, I., et al., Science (2004) 306, 1037-1040) and *Mycobacterium tuberculosis* (Gutierrez, M. G., et al., Cell (2004) 119, 753-766; Harris, J., et al., Immunity (2007) 27, 505-517; Ponpuak, M., et al., Immunity (2010) 32, 329-341), have been extended to a wide variety of microbes with a caveat that most highly adapted pathogens have evolved specific protective mechanisms against autophagic elimination of microbes (Deretic and Levine, 2009; Gannage M. et al., Cell Host Microbe (2009) 6, 367-380; Kyei G. B. et al., J Cell Biol (2009) 186, 255-268; Lee J. S., et al., Nat Cell Biol (2009) 11, 1355-1362; Orvedahl A. et al., Cell Host and Microbe (2007) 1, 23-35; Yoshikawa, Y., et al. Nat Cell Biol (2009) 11, 1233-1240.). Other studies have uncovered orderly intersections between autophagy and innate immunity (Chaturvedi, A., et al., Dorward, D., and Pierce, S. K., Immunity (2008) 28, 799-809; Cooney, R., et al., Nat Med (2010) 16, 90-97; Delgado, M. A., et al., Embo J (2008) 27, 1110-1121; Huang, J., Proc Natl Acad Sci USA (2009) 106(15):6226-31; Sanjuan, M. A., et al., Nature (2007) 450, 1253-1257; Shi, C. S., and Kehrl, J. H., Sci Signal (2010) 3, ra42; Singh, S. B., Davis, A. S., Taylor, G. A., and Deretic, V., Science (2006) 313, 1438-1441; Tang, D., et al., J Cell Biol (2010) 190, 881-892; Travassos, L. H., et al. Nat Immunol (2010) 11, 55-62; Xu, Y., Jagannath, C., et al., Immunity (2007) 27, 135-144; Yano, T., Mita, S., Ohmori, H., Oshima, Y., Fujimoto, Y., Ueda, R., Takada, H., Goldman, W. E., Fukase, K., Silverman, N., et al., Nat Immunol (2008) 9, 908-916.), adaptive immunity (Blanchet, F. P., et al., Immunity (2010) 32, 654-669; Lee, H. K., et al., Immunity (2010) 32, 227-239; Munz, C. (2009). Enhancing immunity through autophagy. Annu Rev Immunol 27, 423-449; Nedjic, J., et al., Nature (2009) 455, 396-400; Paludan, C., et al., Science (2005) 307, 593-596), T-cell development, differentiation and homeostasis (Jia, W., and He, Y. W., J Immunol (2011) 186, 5313-5322; Johansen, T., and Lamark, T. (2011).

Autophagy (2011) 7; Nedjic, J., et al., Nature (2008) 455, 396-400), and inflammatory responses (Cadwell, K., et al., Cell (2010) 141, 1135-1145; Jounai, N., et al., Proc Natl Acad Sci USA (2007) 104, 14050-14055; Levine B, et al., Nature (2011) 469: 323-335; Saitoh, T., and Akira, S., J Cell Biol (2010) 189, 925-935). It was also found that autophagy suppresses endogenous, cell-autonomous promoters of inflammation (Mathew, R., et al., Cell (2009) 137, 1062-1075; Orvedahl, A., et al., Cell Host Microbe (2010) 7, 115-127).

Specific autophagic factors, such as Atg5-Atg12, have been shown to inhibit RIG-I signaling (Jounai, N., et al., Proc Natl Acad Sci USA (2007) 104, 14050-14055) whereas Atg9 has been reported to negatively regulate trafficking, assembly and activation of TBK-1 (TANK-binding kinase 1), which, among its key functions, controls type I interferon response elicited by intracellular double stranded DNA (Saitoh, T., et al., Proc Natl Acad Sci USA (2009) 106, 20842-20846). In the context of anti-inflammatory function, recent studies indicate that autophagy plays an inhibitory role in inflammasome and IL-1β activation by mechanisms that involve mitochondrial homeostasis (Nakahira K, et al., Nat Immunol (2010) 12: 222-230; Zhou R, et al., Nature (2011) 469: 221-225) or potentially direct effects (Harris J, et al., J Biol Chem (2011) 286: 9587-9597). Finally, a number of genetic links have been found in human populations between autophagy and idiopathic inflammation (Consortium, Nature (2007) 447, 661-678; Craddock, N., et al. Nature (2010) 464, 713-720.) or infectious diseases such as tuberculosis (Che, N., et al., Clin Chim Acta (2010) 411, 1645-1649; Intemann, C. D., et al., PLoS Pathog (2009) 5, e1000577; Singh, S. B., et al., Science (2006) 313, 1438-1441; Singh, S. B., et al., Nat Cell Biol (2010) 12, 1154-1165), with significant inflammatory components and tissue damage.

Given the interconnectedness of autophagy and immunity, it is likely that the immune manifestations of autophagy are affected not only by the induction of autophagy but also by the completion of the autophagic pathway. The formation of the autophagic organelles of the sensu stricto autophagy pathway (also referred to as macroautophagy) depends on multiple sources of membrane or regulatory factors (Tooze, S. A., and Yoshimori, T., Nat Cell Biol (2010) 12, 831-835). The key stages of autophagy, however, are not restricted to the formation of autophagosomal membranes and include the sequestration of the earmarked cargo by the autophagic adaptors (Bjorkoy, G., et al., J Cell Biol (2005) 171, 603-614; Kirkin, V., et al. Mol Cell (2009) 33, 505-516; Thurston, T. L., et al., Nat Immunol (2009) 10, 1215-1221; Wild, P., et al., Science (2011) 333, 228-233), and the less understood process of the maturation of autophagic organelles into autolysosomes where the captured material is degraded (Liang, C., et al., Nat Cell Biol (2008) 10, 776-787; Matsunaga, K., et al. Nat Cell Biol (2009) 11, 385-396).

Autophagy is directly implicated in cancer, type II diabetes, neurodegenerative syndromes such as Alzheimer's, Huntington's and Parkinson's diseases, chronic inflammatory diseases (e.g. Crohn's disease), type II diabetes, infections (such as tuberculosis and HIV (I and II)/AIDS, hepatitis B, hepatitis C), and a variety of disorders associated with aging. A better understanding of how autophagic mechanisms are implicated in the aforementioned diseases could prove critical to preventing or treating these maladies.

SUMMARY

The elucidation of certain autophagic processes involved in the onset and progression of a variety of infectious, inflammatory, developmental, chronic pain, and depression-related disorders has led to the discovery of compounds and methods to treat and diagnose such ailments. Further, the compounds are effective as modulators of autophagy in the treatment of infectious, inflammatory, developmental, chronic pain, and depression-related disorders, as well as being used in analyses of autophagic processes, including the disease state in a patient for diagnosis and/or monitoring therapy of the disease state. The present invention is directed to compounds which exhibit biological activity as modulators (inhibitors or agonists) of autophagy and consequently can be used in the treatment of diseases which occur or are mediated through autophagy.

In one embodiment, the present invention provides novel compounds. The compounds can be used to treat a subject, for example, to modulate autophagy. In this aspect of the invention, a compound identified herein as an autophagy modulator (inhibitor or agonist, also referred to generically as an "autostatin") is presented to the biological system, including administration to a patient or subject in need, in order to modulate (often enhance or up-regulate but in certain instances, to inhibit) autophagy and effect a favorable result in the biological system. The resulting modulation may be monitored or applied in the biological system to effect a favorable result, including the inhibition, treatment and/or prevention of cancer, including metastasis of cancer, or the inhibition, treatment (including the amelioration of symptoms), and/or prevention of one or more disease states or conditions in which the modulation, especially including upregulation or inhibition of autophagy provides a favorable result in numerous disease states and/or conditions including neurodegeneration (including, for example, Alzheimer's disease, Parkinson's disease; other ataxias), chronic inflammatory diseases (including, for example, inflammatory bowel disease, including Crohn's disease, rheumatoid arthritis, lupus, multiple sclerosis, chronic obstructive pulmonary disease/COPD, pulmonary fibrosis, cystic fibrosis, Sjogren's disease), diabetes and metabolic syndrome, muscle degeneration and atrophy, frailty in aging, stroke and spinal cord injury, arteriosclerosis, infectious diseases (HIV, HBV, HCV, including secondary associated disease states or conditions, including AIDS) and tuberculosis, among others, and chronic pain related disorders (including, for example, chronic joint pain, chronic back pain, chronic nerve pain, chronic headaches, trigeminal pain, myofascial pain syndrome/MPS, fibromyalgia), and depressive conditions (including, for example, post-traumatic stress disorder/PTSD, chronic pain syndrome/CPS, chronic regional pain syndrome/CRPS) and related disorders, and developmental diseases (both overly mature and immature development, including erythrocyte differentiation, embryogenesis/fertility and ageing/progeria). The common principle of this embodiment of the invention is that compounds, including autostatins which are autophagy modulators, depending upon the disease state, condition or symptom to be treated, may cure, prevent (including reducing the likelihood of), improve prognosis, ameliorate symptoms and/or improve the quality of the patient's or subject's life. In addition, in the therapeutic aspects of the invention, the administration of the compound of the invention may prolong the life of the patient, as well as improve the quality of life in the aging patient or subject.

The compound of the invention can be used to treat an autophagy-mediated disease alone or in combination with at least one autostatin or bioactive agent. An autostatin such as, for example, flubendazole, hexachlorophene, propidium iodide, bepridil, clomiphene citrate (Z,E), GBR 12909, propafenone, metixene, dipivefrin, fluvoxamine, dicyclomine, dimethisoquin, ticlopidine, memantine, bromhexine, norcyclobenzaprine, diperodon, nortriptyline, tetrachlorisophthalonitrile and phenylmercuric acetate, benzethonium, niclosamide, monensin, bromperidol, levobunolol, dehydroisoandosterone 3-acetate, sertraline, tamoxifen, reserpine, hexachlorophene, dipyridamole, harmaline, prazosin, lidoflazine, thiethylperazine, dextromethorphan, desipramine, mebendazole, canrenone, chlorprothixene, maprotiline, homochlorcyclizine, loperamide, nicardipine, dexfenfluramine, nilvadipine, dosulepin, biperiden, denatonium, etomidate, toremifene, tomoxetine, clorgyline, zotepine, beta-escin, tridihexethyl, ceftazidime, methoxy-6-harmalan, melengestrol, albendazole, rimantadine, chlorpromazine, pergolide, cloperastine, prednicarbate, haloperidol, clotrimazole, nitrofural, iopanoic acid, naftopidil, methimazole, trimeprazine, ethoxyquin, clocortolone, doxycycline, pirlindole mesylate, doxazosin, deptropine, nocodazole, scopolamine, oxybenzone, halcinonide, oxybutynin, miconazole, clomipramine, cyproheptadine, doxepin, dyclonine, salbutamol, flavoxate, amoxapine, fenofibrate, pimethixene, pharmaceutically acceptable salts thereof and mixtures thereof, can be administered to a patient or subject in need to treat an autophagy-mediated disease state and/or condition. The autostatin can be either an agonist or inducer of autophagy, or an antagonist or inhibitor of autophagy. The compounds of the invention can be used as modulators of autophagy in the various autophagy-mediated disease states and conditions described herein, with the agonists being preferred in most disease states other than cancer and in the case of the treatment of cancer, the inhibitors described above are preferred, alone or in combination with an autophagy agonist as described above and/or an additional anticancer agent as otherwise described herein.

The additional bioactive agent can be, for example, an anticancer agent, antibiotic, anti-tuberculosis agent, antiviral agent such as an anti-HIV agent, anti-HBV agent or anti-HCV agent. Additionally, at least one anticancer agent can be administered in combination with the compound of the invention. In the present invention, an autostatin may be combined with an additional autophagy modulator.

The present invention also relates to compounds which can be used for the treatment of an autophagy mediated disease state or condition. Thus, the present invention is also directed to pharmaceutical compositions which comprise an effective amount of at least one compound described herein, either alone or in combination with a pharmaceutically acceptable carrier, additive or excipient, an autostatin, at least one additional bioactive agent. Such disease states or conditions, include, for example, cancer, including metastasis of cancer, lysosomal storage diseases, neurodegeneration (including, for example, Alzheimer's disease, Parkinson's disease; other ataxias), immune response, chronic inflammatory diseases, including inflammatory bowel disease, including Crohn's disease, rheumatoid arthritis, lupus, multiple sclerosis, chronic obstructive pulmonary disease/COPD, pulmonary fibrosis, cystic fibrosis, Sjogren's disease; diabetes (I and II) and metabolic syndrome, liver disease, renal disease (including glomerular disease), cardiovascular disease (especially including ischemia, stroke, pressure overload and complications during reperfusion), muscle degeneration and atrophy, frailty in aging, stroke and spinal cord injury, arteriosclerosis, infectious diseases (microbial infections, including bacterial, fungal, cellular and viral, including secondary disease states or conditions associated with infectious diseases), including AIDS and tuberculosis, among others, developmental disease (both overly mature and immature development, including erythrocyte differentiation, embryogenesis/fertility and ageing/progeria), and chronic pain related disorders (including, for example, chronic joint pain, chronic back pain, chronic nerve pain, chronic headaches, trigeminal pain, myofascial pain syndrome/MPS, fibromyalgia), and depressive conditions (including, for example, post-traumatic stress disorder/ PTSD, chronic pain syndrome/CPS, chronic regional pain syndrome/CRPS) and related disorders. The common principle of this embodiment of the invention is that compounds of the invention may be used for the treatment of the disease state and/or condition which is mediated through autophagy.

DETAILED DESCRIPTION

It is noted that, as used in this specification and the appended claims, the singular forms "a," "an," and "the," include plural referents unless expressly and unequivocally limited to one referent. Thus, for example, reference to "a compound" includes two or more different compound. As used herein, the term "include" and its grammatical variants are intended to be non-limiting, such that recitation of items in a list is not to the exclusion of other like items that can be substituted or other items that can be added to the listed items.

The term "compound" or "agent," as used herein, refers to any specific chemical compound disclosed herein and includes tautomers, regioisomers, geometric isomers as applicable, and also where applicable, optical isomers (e.g. enantiomers) thereof, as well as pharmaceutically acceptable salts thereof. Within its use in context, the term compound generally refers to a single compound, but also may include other compounds such as stereoisomers, regioisomers and/or optical isomers (including racemic mixtures) as well as specific enantiomers or enantiomerically enriched mixtures of disclosed compounds as well as diastereomers and epimers, where applicable in context. The term also refers, in context to prodrug forms of compounds which have been modified to facilitate the administration and delivery of compounds to a site of activity.

The term "patient" or "subject" is used throughout the specification within context to describe an animal, generally a mammal and preferably a human, to whom treatment, including prophylactic treatment (prophylaxis), with the methods and compositions according to the present invention is provided. For treatment of those conditions or disease states which are specific for a specific animal such as a human patient, the term patient refers to that specific animal, often a human.

The terms "effective" or "pharmaceutically effective" are used herein, unless otherwise indicated, to describe an amount of a compound or composition which, in context, is used to produce or affect an intended result, usually the modulation of autophagy within the context of a particular treatment or alternatively, the effect of a bioactive agent which is coadministered with the autophagy modulator (autotoxin) in the treatment of disease.

The terms "treat," "treating," and "treatment," as used herein, refer to any action providing a benefit to a patient at risk for or afflicted by an autophagy mediated disease state or condition. The benefit may be in curing the disease state or condition, inhibition of its progression, or ameliorating, lessening or suppressing one or more symptoms of an autophagy mediated disease state or condition. Treatment encompasses both prophylactic and therapeutic treatment.

As used herein, the term "autophagy mediated disease state or condition" refers to a disease state or condition that results from disruption in autophagy or cellular self-digestion. Autophagy is a cellular pathway involved in protein and organelle degradation, and has a large number of connections to human disease. Autophagic dysfunction is associated with cancer, neurodegeneration, microbial infection and ageing, among numerous other disease states and/or conditions. Although autophagy plays a principal role as a protective process for the cell, it also plays a role in cell death. Disease states and/or conditions which are mediated through autophagy (which refers to the fact that the disease state or condition may manifest itself as a function of the increase or decrease in autophagy in the patient or subject to be treated and treatment requires administration of an inhibitor or agonist of autophagy in the patient or subject) include, for example, cancer, including metastasis of cancer, lysosomal storage diseases, neurodegeneration (including, for example, Alzheimer's disease, Parkinson's disease; other ataxias), immune response (T cell maturation, B cell and T cell homeostasis, counters damaging inflammation) and chronic inflammatory diseases (may promote excessive cytokines when autophagy is defective), including, for example, inflammatory bowel disease, including Crohn's disease, rheumatoid arthritis, lupus, multiple sclerosis, chronic obstructive pulmonary disease/COPD, pulmonary fibrosis, cystic fibrosis, Sjogren's disease, hyperglycemic disorders, diabetes (I and II), affecting lipid metabolism islet function and/or structure, excessive autophagy may lead to pancreatic β-cell death and related hyperglycemic disorders, including severe insulin resistance, hyperinsulinemia, insulin-resistant diabetes (e.g. Mendenhall's Syndrome, Werner Syndrome, leprechaunism, and lipoatrophic diabetes) and dyslipidemia (e.g. hyperlipidemia as expressed by obese subjects, elevated low-density lipoprotein (LDL), depressed high-density lipoprotein (HDL), and elevated triglycerides) and metabolic syndrome, liver disease (excessive autophagic removal of cellular entities-endoplasmic reticulum), renal disease (apoptosis in plaques, glomerular disease), cardiovascular disease (especially including ischemia, stroke, pressure overload and complications during reperfusion), muscle degeneration and atrophy, frailty in aging, stroke and spinal cord injury, arteriosclerosis, infectious diseases (microbial infections, removes microbes, provides a protective inflammatory response to microbial products, limits adaptation of autophagy of host by microbe for enhancement of microbial growth, regulation of innate immunity) including bacterial, fungal, cellular and viral (including secondary disease states or conditions associated with infectious diseases), including AIDS and tuberculosis, among others, and chronic pain related disorders (including, for example, chronic joint pain, chronic back pain, chronic nerve pain, chronic headaches, trigeminal pain, myofascial pain syndrome/MPS, fibromyalgia), and depressive conditions (including, for example, post-traumatic stress disorder/ PTSD, chronic pain syndrome/CPS, chronic regional pain syndrome/CRPS) and related disorders. development (including erythrocyte differentiation), embryogenesis/fertility/ infertility (embryo implantation and neonate survival after termination of transplacental supply of nutrients, removal of dead cells during programmed cell death) and ageing (increased autophagy leads to the removal of damaged organelles or aggregated macromolecules to increase health and prolong life, but increased levels of autophagy in children/young adults may lead to muscle and organ wasting resulting in ageing/progeria).

The term "lysosomal storage disorder" refers to a disease state or condition that results from a defect in lysosomal storage. These disease states or conditions generally occur when the lysosome malfunctions. Lysosomal storage disorders are caused by lysosomal dysfunction, usually as a consequence of deficiency of a single enzyme required for the metabolism of lipids, glycoproteins or mucopolysaccharides. The incidence of lysosomal storage disorder (collectively) occurs at an incidence of about 1:5,000-1:10,000. The lysosome is commonly referred to as the cell's recycling center because it processes unwanted material into substances that the cell can utilize. Lysosomes break down this unwanted matter via high specialized enzymes. Lysosomal disorders generally are triggered when a particular enzyme exists in too small an amount or is missing altogether. When this happens, substances accumulate in the cell. In other words, when the lysosome doesn't function normally, excess products destined for breakdown and recycling are stored in the cell. Lysosomal storage disorders are genetic diseases, but these may be treated using autophagy modulators as described herein.

Examples of lysosomal storage disease include, for example, activator deficiency/GM2 gangliosidosis, alpha-mannosidosis, aspartylglucoaminuria, cholesteryl ester storage disease, chronic hexosaminidase A deficiency, cystinosis, Danon disease, Fabry disease, Farber disease, fucosidosis, galactosialidosis, Gaucher Disease (Types I, II and III), GM1 Ganliosidosis, including infantile, late infantile/juvenile and adult/chronic), Hunter syndrome (MPS II), I-Cell disease/Mucolipidosis II, Infantile Free Sialic Acid Storage Disease (ISSD), Juvenile Hexosaminidase A Deficiency, Krabbe disease, Lysosomal acid lipase deficiency, Metachromatic Leukodystrophy, Hurler syndrome, Scheie syndrome, Hurler-Scheie syndrome, Sanfilippo syndrome, Morquio Type A and B, Maroteaux-Lamy, Sly syndrome, mucolipidosis, multiple sulfate deficiency, Niemann-Pick disease, Neuronal ceroid lipofuscinoses, CLN6 disease, Jansky-Bielschowsky disease, Pompe disease, pycnodysostosis, Sandhoff disease, Schindler disease, Tay-Sachs and Wolman disease, among others.

The term "modulator of autophagy," "regulator of autophagy" or "autostatin" is used to refer to a compound which functions as an agonist (inducer or up-regulator) or antagonist (inhibitor or down-regulator) of autophagy. Depending upon the disease state or condition, autophagy may be upregulated (and require inhibition of autophagy for therapeutic intervention) or down-regulated (and require upregulation of autophagy for therapeutic intervention). In most instances, in the case of cancer treatment with a modulator of autophagy as otherwise described herein, the autophagy modulator is often an antagonist of autophagy. In the case of cancer, the antagonist (inhibitor) of autophagy may be used alone or combined with an agonist of autophagy.

The compounds of the invention can be used in the treatment of an autophagy mediated disease state or condition as otherwise described herein. The following compounds have been identified and the structures are set forth below.

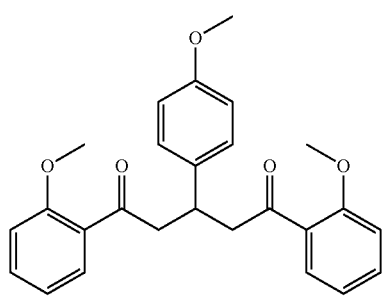 [SMILES: COc1ccc(C(CC(=O)c2ccccc2OC)CC(=O)c2ccccc2OC)cc1]

3-(4-methoxyphenyl)-1,5-bis(2-methoxyphenyl)-1,5-pentanedione

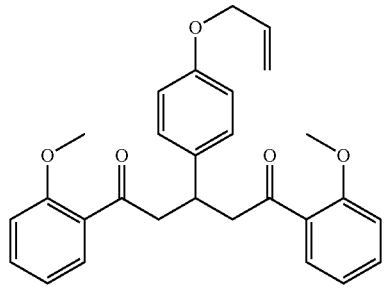 [SMILES: C=CCOc1ccc(C(CC(=O)c2ccccc2OC)CC(=O)c2ccccc2OC)cc1]

3-(4-allyloxyphenyl)-1,5-bis(2-methoxyphenyl)-1,5-pentanedione

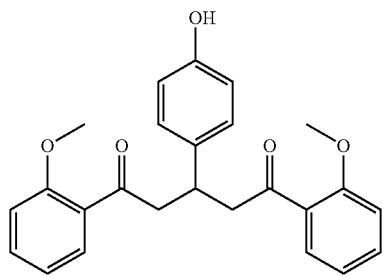 [SMILES: COc1ccccc1C(=O)CC(CC(=O)c1ccccc1OC)c1ccc(O)cc1]

3-(4-hydroxyphenyl)-1,5-bis(2-methoxyphenyl)-1,5-pentanedione

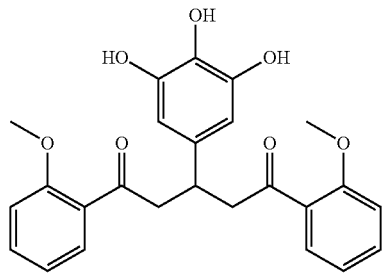 [SMILES: COc1ccccc1C(=O)CC(CC(=O)c1ccccc1OC)c1cc(O)c(O)c(O)c1]

9

3-(3,4,5-trimethoxymethoxyphenyl)-1,5-bis(2-methoxyphenyl)-1,5-pentanedione

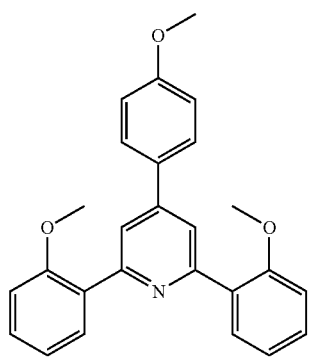 [SMILES: COc1ccc(-c2cc(-c3ccccc3OC)nc(-c3ccccc3OC)c2)cc1]

2,6-di(2-methoxyphenyl)-4-(4-methoxyphenyl) pyridine

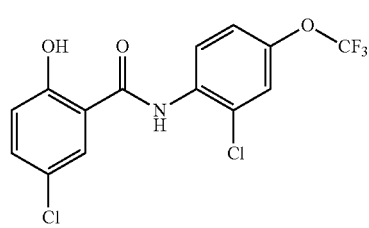 [SMILES: O=C(Nc1ccc(OC(F)(F)F)cc1Cl)c1cc(Cl)ccc1O]

5-Chloro-2-hydroxy-N-(2-chloro-4-trifluoromethyl) phenylbenzamide

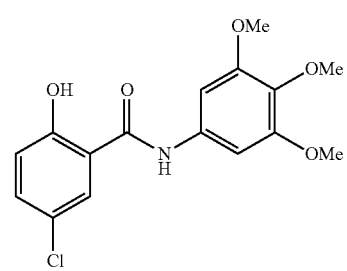 [SMILES: COc1cc(NC(=O)c2cc(Cl)ccc2O)cc(OC)c1OC]

5-Chloro-2-hydroxy-N-(3,4,5-trimethoxy)phenyl-benzamide

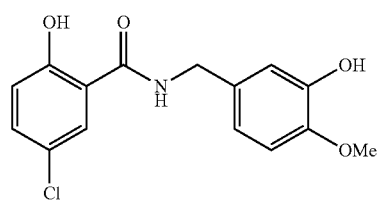 [SMILES: COc1ccc(CNC(=O)c2cc(Cl)ccc2O)cc1O]

10

5-Chloro-2-hydroxy-N-(3-hydroxy-4-methoxy)benzylbenzamide

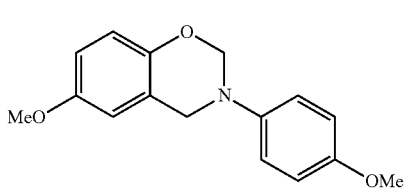 [SMILES: COc1ccc(N2COc3ccc(OC)cc3C2)cc1]

6-Methoxy-3-(4-methoxyphenyl)-3,4-dihydro-2H-1,3-benzoxazine

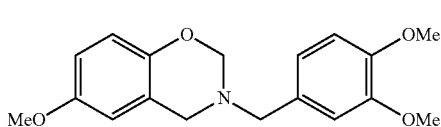 [SMILES: COc1ccc2c(c1)CN(Cc1ccc(OC)c(OC)c1)CO2]

6-Methoxy-3-(4-(3,4-dimethoxybenzyl))-3,4-dihydro-2H-1,3-benzoxazine

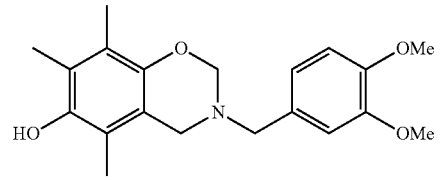 [SMILES: COc1ccc(CN2COc3c(C)c(C)c(O)c(C)c3C2)cc1OC]

6-Methoxy-5,7,8-trimethyl-3-(4-(3,4-dimethoxybenzyl))-3,4-dihydro-2H-1,3-benzoxazine

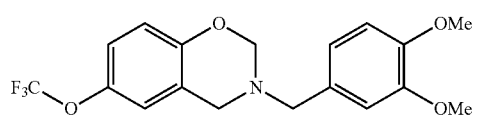 [SMILES: COc1ccc(CN2COc3ccc(OC(F)(F)F)cc3C2)cc1OC]

6-Trifluoromethoxy-3-(4-(3,4-dimethoxybenzyl))-3,4-dihydro-2H-1,3-benzoxazine

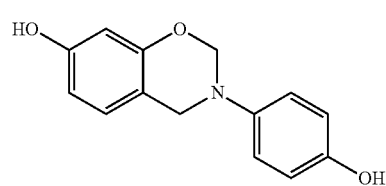 [SMILES: Oc1ccc(N2COc3cc(O)ccc3C2)cc1]

11

7-Hydroxy-3-(4-hydroxyphenyl)-3,4-dihydro-2H-1,3-benzoxazine

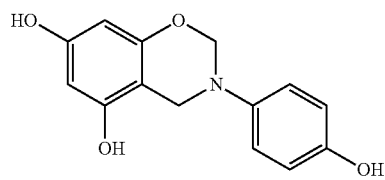 [SMILES: Oc1ccc(N2COc3cc(O)cc(O)c3C2)cc1]

5,7-dihydroxy-3-(4-hydroxyphenyl)-3,4-dihydro-2H-1,3-benzoxazine

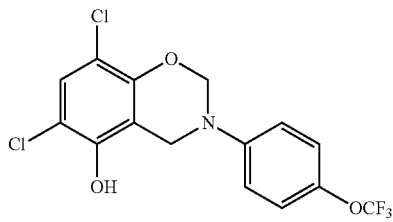 [SMILES: Oc1c(Cl)cc(Cl)c2c1CN(c1ccc(OC(F)(F)F)cc1)CO2]

5-Hydroxy-6,8-dichloro-3-(4-trifluoromethoxyphenyl)-3,4-dihydro-2H-1,3-benzoxazine

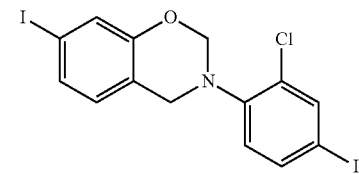 [SMILES: Clc1cc(I)ccc1N1COc2cc(I)ccc2C1]

6-Iodo-3-(2,chloro-4-iodophenyl)-3,4-dihydro-2H-1,3-benzoxazine

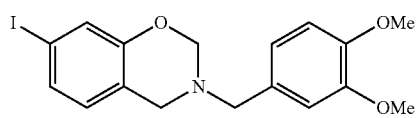 [SMILES: COc1ccc(CN2COc3cc(I)ccc3C2)cc1OC]

7-Iodo-3-(4-(3,4-dimethoxybenzyl))-3,4-dihydro-2H-1,3-benzoxazine

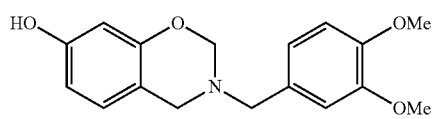

12

7-hydroxy-3-(4-(3,4-dimethoxybenzyl))-3,4-dihydro-2H-1,3-benzoxazine

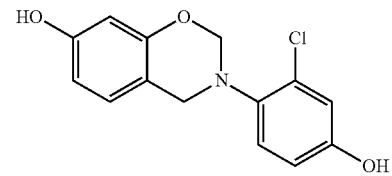 [SMILES: Oc1ccc(N2COc3cc(O)ccc3C2)c(Cl)c1]

6-hydroxy-3-(2-chloro-4-dihydroxyphenyl)-3,4-dihydro-2H-1,3-benzoxazine

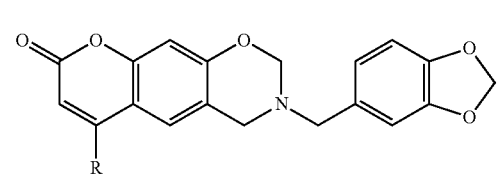

N-benzyl-1,8-Dioxa-3-aza-3,4dihydro-2H-anthracen-7-one series

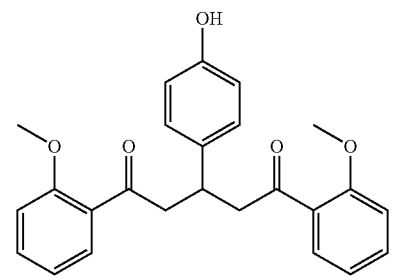 [SMILES: COc1ccccc1C(=O)CC(CC(=O)c1ccccc1OC)c1ccc(O)cc1]

3-(4-hydroxyphenyl)-1,5-bis(2-methoxyphenyl)-1,5-pentanedione

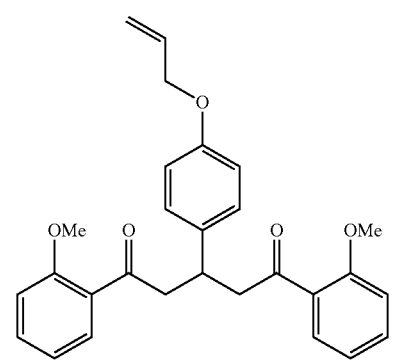 [SMILES: C=CCOc1ccc(C(CC(=O)c2ccccc2OC)CC(=O)c2ccccc2OC)cc1]

13
3-(4-allyloxyphenyl)-1,5-bis(2-methoxyphenyl)-1,5-pentanedione
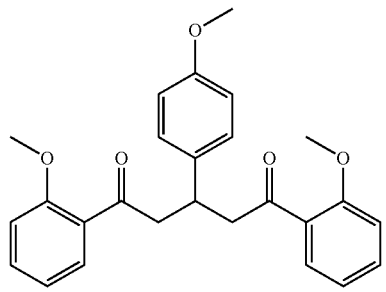 [SMILES: COc1ccc(C(CC(=O)c2ccccc2OC)CC(=O)c2ccccc2OC)cc1]
3-(4-methoxyphenyl)-1,5-bis(2-methoxyphenyl)-1,5-pentanedione
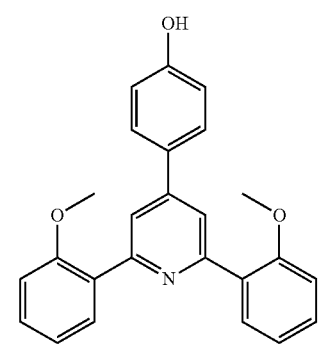 [SMILES: COc1ccccc1-c1cc(-c2ccc(O)cc2)cc(-c2ccccc2OC)n1]
2,6-di(2-methoxyphenyl)-4-(4-hydroxyphenyl)pyridine
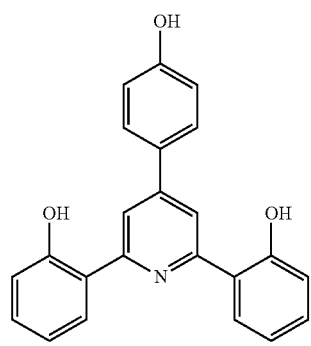 [SMILES: Oc1ccc(-c2cc(-c3ccccc3O)nc(-c3ccccc3O)c2)cc1]
14
2,6-di(2-hydroxyphenyl)-4-(4-hydroxyphenyl)pyridine
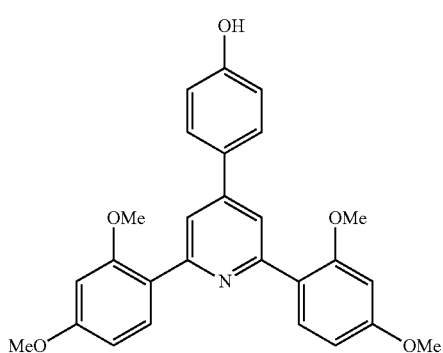 [SMILES: COc1ccc(-c2cc(-c3ccc(O)cc3)cc(-c3ccc(OC)cc3OC)n2)c(OC)c1]
2,6-di(2,4-dimethoxyphenyl)-4-(4-hydroxyphenyl)pyridine
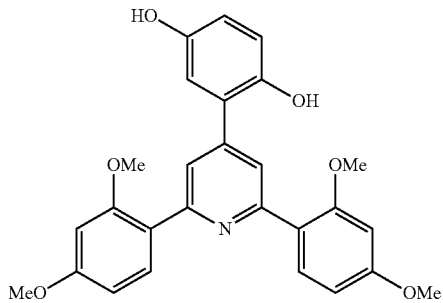 [SMILES: COc1ccc(-c2cc(-c3cc(O)ccc3O)cc(-c3ccc(OC)cc3OC)n2)c(OC)c1]
2,6-di(2,4-dimethoxyphenyl)-4-(2,5-dihydroxyphenyl)pyridine
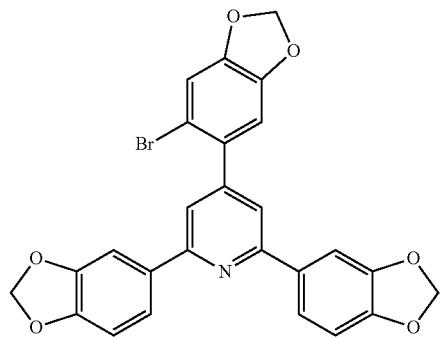 [SMILES: Brc1cc2c(cc1-c1cc(-c3ccc4c(c3)OCO4)nc(-c3ccc4c(c3)OCO4)c1)OCO2]

15
2,6-di(3,4-methylenedioxyphenyl)-4-(2-bromo-4,5-methylenedioxyphenyl)pyridine
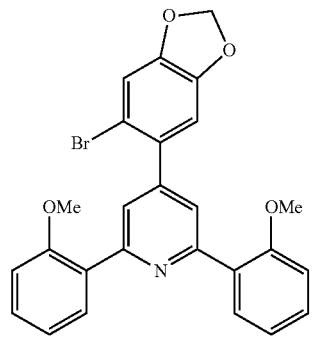 [SMILES: COc1ccccc1-c1cc(-c2cc3c(cc2Br)OCO3)cc(-c2ccccc2OC)n1]
2,6-di(2-methoxyphenyl)-4-(2-bromo-4,5-methylenedioxyphenyl)pyridine
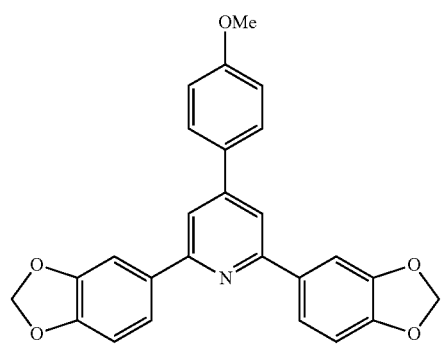 [SMILES: COc1ccc(-c2cc(-c3ccc4c(c3)OCO4)nc(-c3ccc4c(c3)OCO4)c2)cc1]
2,6-di(3,4-methylenedioxyphenyl)-4-(2-methoxyphenyl)pyridine
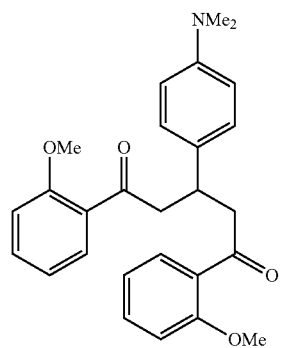 [SMILES: COc1ccccc1C(=O)CC(CC(=O)c1ccccc1OC)c1ccc(N(C)C)cc1]
16
3-(4-dimethylaminophenyl)-1,5-bis(2-methoxyphenyl)-1,5-pentanedione
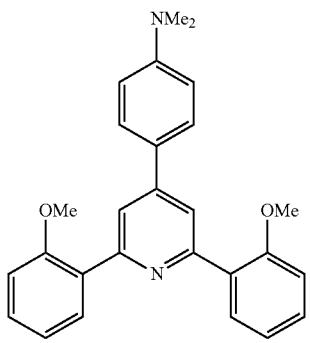 [SMILES: COc1ccccc1-c1cc(-c2ccc(N(C)C)cc2)cc(-c2ccccc2OC)n1]
2,6-di(2-methoxyphenyl)-4-(dimethylaminophenyl)pyridine
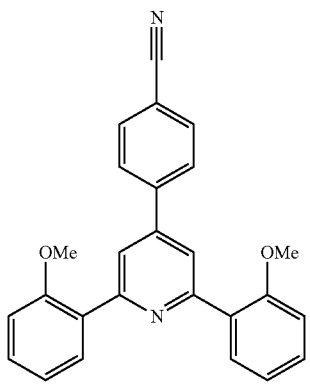 [SMILES: COc1ccccc1-c1cc(-c2ccc(C#N)cc2)cc(-c2ccccc2OC)n1]
2,6-di(2-methoxyphenyl)-4-(4-cyanophenyl)pyridine
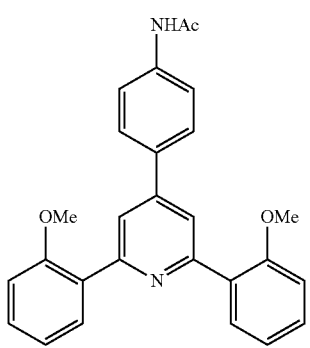 [SMILES: COc1ccccc1-c1cc(-c2ccc(NC(C)=O)cc2)cc(-c2ccccc2OC)n1]

17
2,6-di(2-methoxyphenyl)-4-(4-acetomidophenyl) pyridine
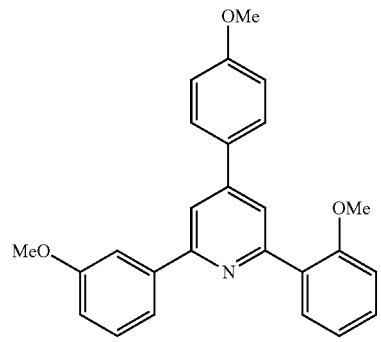 [SMILES: COc1ccc(-c2cc(-c3cccc(OC)c3)nc(-c3ccccc3OC)c2)cc1]
2-(2-methoxyphenyl)-6-(3-methoxyphenyl)-4-(4-methoxyphenyl) pyridine
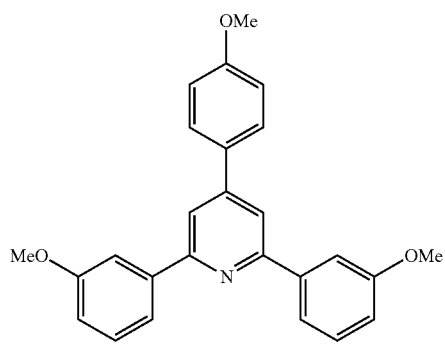 [SMILES: COc1ccc(-c2cc(-c3cccc(OC)c3)nc(-c3cccc(OC)c3)c2)cc1]
2,6-di(3-methoxyphenyl)-4-(4-methoxyphenyl)pyridine
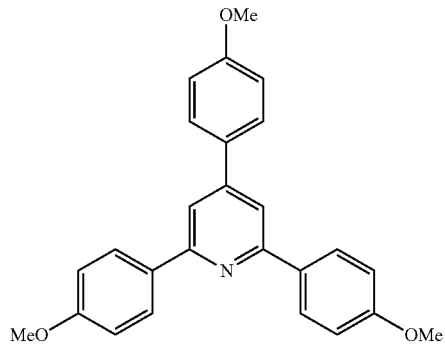 [SMILES: COc1ccc(-c2cc(-c3ccc(OC)cc3)nc(-c3ccc(OC)cc3)c2)cc1]
18
2,6-di(4-methoxyphenyl)-4-(4-methoxyphenyl)pyridine
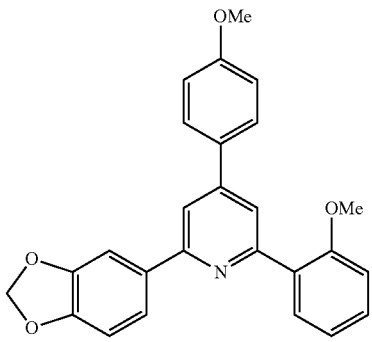 [SMILES: COc1ccc(-c2cc(-c3ccc4c(c3)OCO4)nc(-c3ccccc3OC)c2)cc1]
2-(3,4-methylenedioxy)-6-(2-methoxyphenyl)-4-(4-methoxyphenyl) pyridine
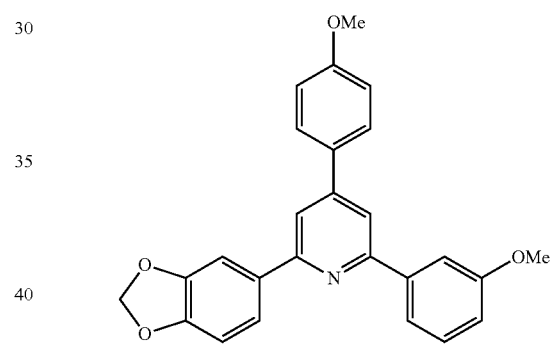
2-(3,4-methylenedioxy)-6-(3-methoxyphenyl)-4-(4-methoxyphenyl) pyridine
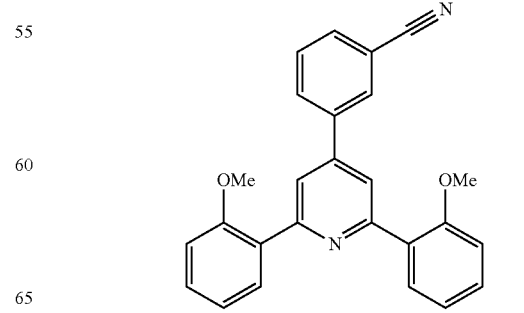

| 19 | 20 |
|---|---|
| 2,6-di(2-methoxyphenyl)-4-(3-cyanophenyl)pyridine | 2-(3-methoxyphenyl)-6-(4-methoxyphenyl)-4-(4-methoxyphenyl) pyridine |
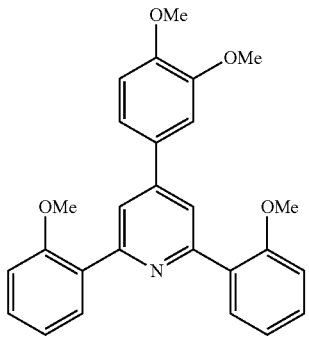 [SMILES: COc1ccc(-c2cc(-c3ccccc3OC)nc(-c3ccccc3OC)c2)cc1OC]
2,6-di(2-methoxyphenyl)-4-(3,4-dimethoxyphenyl) pyridine
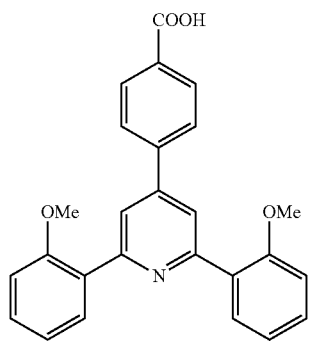
2,6-di(2-methoxyphenyl)-4-(4-carboxyphenyl)pyridine
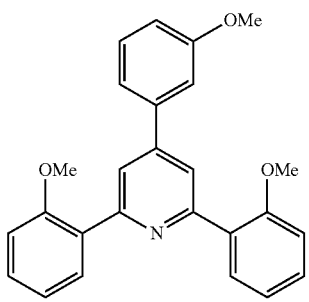 [SMILES: COc1cccc(-c2cc(-c3ccccc3OC)nc(-c3ccccc3OC)c2)c1]
2,6-di(2-methoxyphenyl)-4-(3-methoxyphenyl)pyridine
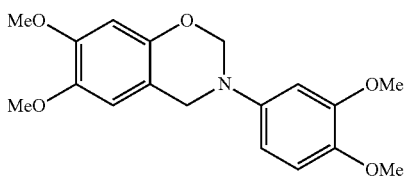 [SMILES: COc1ccc(N2COc3cc(OC)c(OC)cc3C2)cc1OC]
5,6-dimethoxy-3-(4-methoxyphenyl)-3,4-dihydro-2H-1,3-benzoxazine
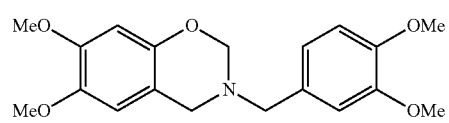 [SMILES: COc1ccc(CN2COc3cc(OC)c(OC)cc3C2)cc1OC]
5,6-dimethoxy-3-(4-methoxybenzyl)-3,4-dihydro-2H-1,3-benzoxazine
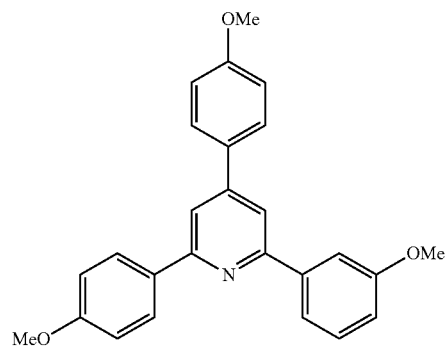
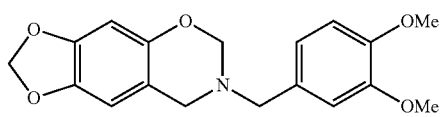 [SMILES: COc1ccc(CN2COc3cc4c(cc3C2)OCO4)cc1OC]

21

5,6-methylenedioxy-3-(4-methoxybenzyl)-3,4-dihydro-2H-1,3-benzoxazine

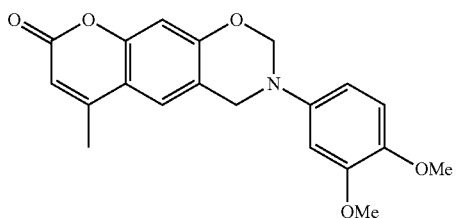 [SMILES: COc1ccc(N2COc3cc4oc(=O)cc(C)c4cc3C2)cc1OC]

N-(3,4-dimethoxypheny)-1,8-Dioxa-3-aza-2,4-dihydro-2H-5-methyl-anthracen-7-one

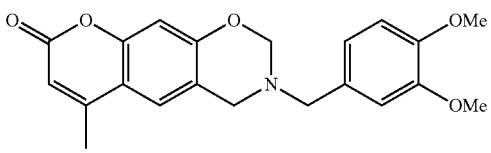 [SMILES: COc1ccc(CN2COc3cc4oc(=O)cc(C)c4cc3C2)cc1OC]

N-(3,4-dimethoxybenzyl)-1,8-Dioxa-3-aza-2,4-dihydro-2H-5-methyl-anthracen-7-one

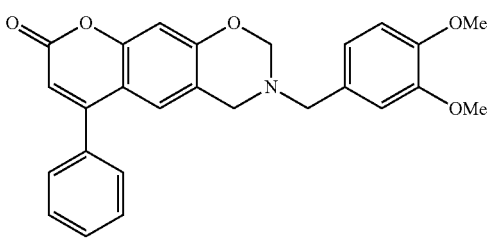 [SMILES: COc1ccc(CN2COc3cc4oc(=O)cc(-c5ccccc5)c4cc3C2)cc1OC]

N-(3,4-dimethoxypheny)-1,8-Dioxa-3-aza-2,4-dihydro-2H-5-phenyl-anthracen-7-one

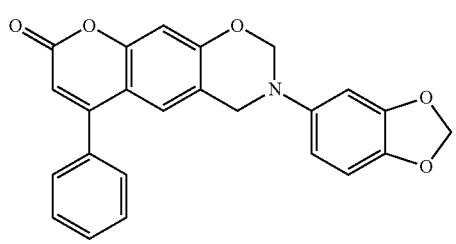 [SMILES: O=c1cc(-c2ccccc2)c2cc3c(cc2o1)OCN(c1ccc2c(c1)OCO2)C3]

22

N-(3,4-methylenedioxypheny)-1,8-Dioxa-3-aza-2,4-dihydro-2H-5-phenyl-anthracen-7-one

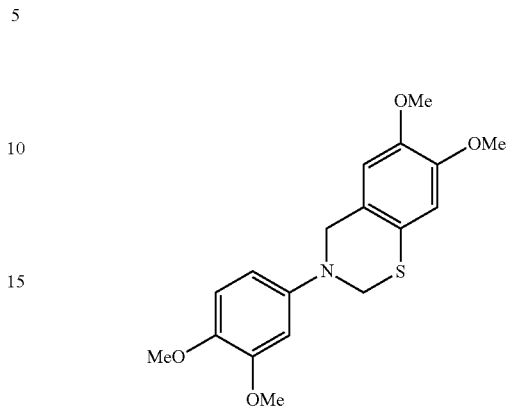

5,6-dimethoxy-3-(4-methoxyphenyl)-3,4-dihydro-2H-1,3-benthiazine

The following compounds share the following backbone:

a) 2,6-di(3,4-methylenedioxyphenyl)-4-(2-bromo-4,5-methylenedioxyphenyl)pyridine
b) 2,6-di(3,4-methylenedioxyphenyl)-4-(2-methoxyphenyl) pyridine
c) 2,6-di(2-methoxyphenyl)-4-(4-methoxyphenyl) pyridine
d) 2,6-di(2-methoxyphenyl)-4-(4-hydroxyphenyl)pyridine
e) 2,6-di(2-methoxyphenyl)-4-(2-bromo-4,5-methylenedioxyphenyl)pyridine
f) 2,6-di(2-methoxyphenyl)-4-(3-methoxyphenyl)pyridine
g) 2,6-di(2-methoxyphenyl)-4-(4-acetomidophenyl)pyridine
h) 2,6-di(2-methoxyphenyl)-4-(4-cyanophenyl) pyridine
i) 2,6-di(2-methoxyphenyl)-4-(3-cyanophenyl)pyridine
j) 2,6-di(2-methoxyphenyl)-4-(4-carboxyphenyl)pyridine
k) 2,6-di(2-methoxyphenyl)-4-(3,4-dimethoxyphenyl)pyridine
l) 2,6-di(2-methoxyphenyl)-4-(dimethylaminophenyl)pyridine
m) 2-(2-methoxyphenyl)-6-(3-methoxyphenyl)-4-(4-methoxyphenyl) pyridine
n) 2,6-di(4-methoxyphenyl)-4-(4-methoxyphenyl)pyridine
o) 2,6-di(3-methoxyphenyl)-4-(4-methoxyphenyl)pyridine
p) 2,6-di(2-hydroxyphenyl)-4-(4-hydroxyphenyl)pyridine
q) 2,6-di(2,4-dimethoxyphenyl)-4-(4-hydroxyphenyl)pyridine
r) 2,6-di(2,4-dimethoxyphenyl)-4-(2,5-dihydroxyphenyl) pyridine
s) 2-(3,4-methylenedioxy)-6-(3-methoxyphenyl)-4-(4-methoxyphenyl) pyridine
t) 2-(3-methoxyphenyl)-6-(4-methoxyphenyl)-4-(4-methoxyphenyl) pyridine
u) 2-(3,4-methylenedioxy)-6-(2-methoxyphenyl)-4-(4-methoxyphenyl) pyridine

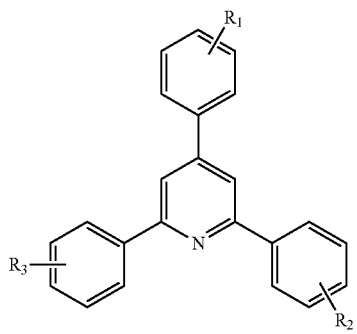

The following compounds share the following backbone:
a) N-(3,4-dimethoxypheny)-1,8-Dioxa-3-aza-2,4-dihydro-2H-5-phenyl-anthracen-7-one
b) N-(3,4-dimethoxybenzyl)-1,8-Dioxa-3-aza-2,4-dihydro-2H-5-methyl-anthracen-7-one
c) N-benzyl-1,8-Dioxa-3-aza-3,4dihydro-2H-anthracen-7-one series
d) N-(3,4-dimethoxypheny)-1,8-Dioxa-3-aza-2,4-dihydro-2H-5-methyl-anthracen-7-one

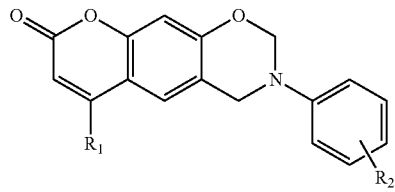

The following compounds share the following backbone:
a) 7-hydroxy-3-(4-(3,4-dimethoxybenzyl))-3,4-dihydro-2H-1,3-benzoxazine
b) 5,6-dimethoxy-3-(4-methoxybenzyl)-3,4-dihydro-2H-1,3-benzoxazine
c) 7-Iodo-3-(4-(3,4-dimethoxybenzyl))-3,4-dihydro-2H-1,3-benzoxazine
d) 6-Methoxy-3-(4-(3,4-dimethoxybenzyl))-3,4-dihydro-2H-1,3-benzoxazine
e) 6-Methoxy-5,7,8-trimethyl-3-(4-(3,4-dimethoxybenzyl))-3,4-dihydro-2H-1,3-benzoxazine
f) 5,6-methylenedioxy-3-(4-methoxybenzyl)-3,4-dihydro-2H-1,3-benzoxazine
g) 6-Trifluoromethoxy-3-(4-(3,4-dimethoxybenzyl))-3,4-dihydro-2H-1,3-benzoxazine
h) 7-Hydroxy-3-(4-hydroxyphenyl)-3,4-dihydro-2H-1,3-benzoxazine
i) 6-Methoxy-3-(4-methoxyphenyl)-3,4-dihydro-2H-1,3-benzoxazine
j) 5-Hydroxy-6,8-dichloro-3-(4-trifluoromethoxyphenyl)-3,4-dihydro-2H-1,3-benzoxazine
k) 5,7-dihydroxy-3-(4-hydroxyphenyl)-3,4-dihydro-2H-1,3-benzoxazine
l) 6-hydroxy-3-(2-chloro-4-dihydroxyphenyl)-3,4-dihydro-2H-1,3-benzoxazine
m) 6-Iodo-3-(2,chloro-4-iodophenyl)-3,4-dihydro-2H-1,3-benzoxazine
n) 5,6-dimethoxy-3-(4-methoxyphenyl)-3,4-dihydro-2H-1,3-benzoxazine
o) 5,6-dimethoxy-3-(4-methoxyphenyl)-3,4-dihydro-2H-1,3-benthiazine

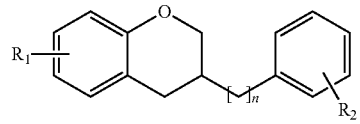

The following compounds share the following backbone:
a) 5-Chloro-2-hydroxy-N-(3-hydroxy-4-methoxy)benzyl-benzamide
b) 5-Chloro-2-hydroxy-N-(2-chloro-4-trifluoromethyl) phenylbenzamide
c) 5-Chloro-2-hydroxy-N-(3,4,5-trimethoxy)phenylbenzamide

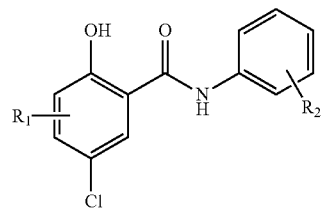

The following compounds share the following backbone:
a) 3-(4-methoxyphenyl)-1,5-bis(2-methoxyphenyl)-1,5-pentanedione
b) 3-(4-hydroxyphenyl)-1,5-bis(2-methoxyphenyl)-1,5-pentanedione
c) 3-(4-methoxyphenyl)-1,5-bis(2-methoxyphenyl)-1,5-pentanedione
d) 3-(4-allyloxyphenyl)-1,5-bis(2-methoxyphenyl)-1,5-pentanedione
e) 3-(4-hydroxyphenyl)-1,5-bis(2-methoxyphenyl)-1,5-pentanedione
f) 3-(3,4,5-trimethoxymethoxyphenyl)-1,5-bis(2-methoxyphenyl)-1,5-pentanedione
g) 3-(4-allyloxyphenyl)-1,5-bis(2-methoxyphenyl)-1,5-pentanedione
h) 3-(4-dimethylaminophenyl)-1,5-bis(2-methoxyphenyl)-1,5-pentanedione

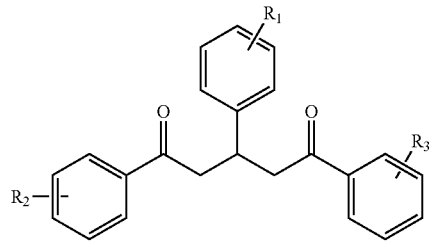

These compounds, their analogs and pharmaceutically acceptable salts thereof can be used as modulators of autophagy in various autophagy-mediated disease states and conditions described herein, with the agonists being preferred in most disease states other than cancer (although inhibitors may also be used alone, or preferably in combination with the agonists) In the case of the treatment of cancer, the inhibitors described above are preferred, alone or in combination with an autophagy agonist as described above and/or an additional anticancer agent as otherwise described herein.

Other compounds which may be used in combination with the compounds of the invention include, for example, other "additional autophagy modulators" or "additional autostatins" which are known in the art. These can be combined with one or more of the compounds to provide novel pharmaceutical compositions and/or methods of treating autophagy mediated disease states and conditions which are otherwise described herein. These additional autophagy modulators include, for example, benzethonium, niclosamide, monensin, bromperidol, levobunolol, dehydroisoandosterone 3-acetate, sertraline, tamoxifen, reserpine, hexachlorophene, dipyridamole, harmaline, prazosin, lidoflazine, thiethylperazine, dextromethorphan, desipramine, mebendazole, canrenone, chlorprothixene, maprotiline, homochlorcyclizine, loperamide, nicardipine, dexfenfluramine, nilvadipine, dosulepin, biperiden, denatonium, etomidate, toremifene, tomoxetine, clorgyline, zotepine, beta-escin, tridihexethyl, ceftazidime, methoxy-6-harmalan, melengestrol, albendazole, rimantadine, chlorpromazine, pergolide, cloperastine, prednicarbate, haloperidol, clotrimazole, nitrofural, iopanoic acid, naftopidil, Methimazole, Trimeprazine, Ethoxyquin, Clocortolone, Doxycycline, Pirlindole mesylate, Doxazosin, Deptropine, Nocodazole, Scopolamine, Oxybenzone, Halcinonide, Oxybutynin, Miconazole, Clomipramine, Cyproheptadine, Doxepin, Dyclonine, Salbutamol, Flavoxate, Amoxapine, Fenofibrate, Pimethixene and mixtures thereof.

The term "co-administration" or "combination therapy" is used to describe a therapy in which at least two compounds in effective amounts are used to treat an autophagy mediated disease state or condition as otherwise described herein, either at the same time or within dosing or administration schedules ascertainable by those of ordinary skill in the art. Although the term co-administration preferably includes the administration of two active compounds to the patient at the same time, it is not necessary that the compounds be administered to the patient at the same time, although effective amounts of the individual compounds will be present in the patient at the same time. In addition, in certain embodiments, co-administration will refer to the fact that two compounds are administered at significantly different times, but the effects of the two compounds are present at the same time. Thus, the term co-administration includes an administration in which one active agent (especially an autophagy modulator) is administered at approximately the same time (contemporaneously), or from about one to several minutes to about 24 hours or more than the other bioactive agent coadministered with the autophagy modulator. The additional bioactive agent may be any bioactive agent, but is generally selected from an additional autophagy mediated compound, an additional anticancer agent, or another agent, such as a mTOR inhibitor such as pp242, rapamycin, envirolimus, everolimus or cidaforollimus, among others including epigallocatechin gallate (EGCG), caffeine, curcumin or reseveratrol (which mTOR inhibitors find particular use as enhancers of autophagy using the compounds disclosed herein and in addition, in the treatment of cancer with an autophagy modulator (inhibitor) as described herein, including in combination with tetrachlorisophthalonitrile, phenylmercuric acetate and their pharmaceutically acceptable salts, which are inhibitors of autophagy. It is noted that in the case of the treatment of cancer, the use of an autophagy inhibitor is preferred, alone or in combination with an autophagy inducer (agonist) as otherwise described herein and/or a mTOR inhibitor as described above. In certain embodiments, an mTOR inhibitor selected from the group consisting of pp242, rapamycin, envirolimus, everolimus, cidaforollimus, epigallocatechin gallate (EGCG), caffeine, curcumin, reseveratrol and mixtures thereof may be combined with at least one agent selected from the group consisting of digoxin, xylazine, hexetidine and sertindole, the combination of such agents being effective as autophagy modulators.

The term "cancer" is used throughout the specification to refer to the pathological process that results in the formation and growth of a cancerous or malignant neoplasm, i.e., abnormal tissue that grows by cellular proliferation, often more rapidly than normal and continues to grow after the stimuli that initiated the new growth cease. Malignant neoplasms show partial or complete lack of structural organization and functional coordination with the normal tissue and most invade surrounding tissues, metastasize to several sites, and are likely to recur after attempted removal and to cause the death of the patient unless adequately treated.

As used herein, the term neoplasia is used to describe all cancerous disease states and embraces or encompasses the pathological process associated with malignant hematogenous, ascitic and solid tumors. Representative cancers include, for example, stomach, colon, rectal, liver, pancreatic, lung, breast, cervix uteri, corpus uteri, ovary, prostate, testis, bladder, renal, brain/CNS, head and neck, throat, Hodgkin's disease, non-Hodgkin's lymphoma, multiple myeloma, leukemia, melanoma, non-melanoma skin cancer (especially basal cell carcinoma or squamous cell carcinoma), acute lymphocytic leukemia, acute myelogenous leukemia, Ewing's sarcoma, small cell lung cancer, choriocarcinoma, rhabdomyosarcoma, Wilms' tumor, neuroblastoma, hairy cell leukemia, mouth/pharynx, esophagus, larynx, kidney cancer and lymphoma, among others, which may be treated by one or more compounds according to the present invention. In certain aspects, the cancer which is treated is lung cancer, breast cancer, ovarian cancer and/or prostate cancer.

The term "tumor" is used to describe a malignant or benign growth or tumefacent.

The term "additional anti-cancer compound," "additional anti-cancer drug" or "additional anti-cancer agent" is used to describe any compound (including its derivatives) which may be used to treat cancer. The "additional anti-cancer compound," "additional anti-cancer drug" or "additional anti-cancer agent" can be an anticancer agent which is distinguishable from a CIAE-inducing anticancer ingredient such as a taxane, vinca alkaloid and/or radiation sensitizing agent otherwise used as chemotherapy/cancer therapy agents herein. In many instances, the co-administration of another anti-cancer compound according to the present invention results in a synergistic anti-cancer effect. Exemplary anti-cancer compounds for co-administration with formulations according to the present invention include anti-metabolites agents which are broadly characterized as antimetabolites, inhibitors of topoisomerase I and II, alkylating agents and microtubule inhibitors (e.g., taxol), as well as tyrosine kinase inhibitors (e.g., surafenib), EGF kinase inhibitors (e.g., tarceva or erlotinib) and tyrosine kinase inhibitors or ABL kinase inhibitors (e.g. imatinib).

Anti-cancer compounds for co-administration include, for example, Aldesleukin; Alemtuzumab; alitretinoin; allopurinol; altretamine; amifostine; anastrozole; arsenic trioxide; Asparaginase; BCG Live; bexarotene capsules; bexarotene gel; bleomycin; busulfan intravenous; busulfan oral; calusterone; capecitabine; carboplatin; carmustine; carmustine with Polifeprosan 20 Implant; celecoxib; chlorambucil; cisplatin; cladribine; cyclophosphamide; cytarabine; cytarabine liposomal; dacarbazine; dactinomycin; actinomycin D;

Darbepoetin alfa; daunorubicin liposomal; daunorubicin, daunomycin; Denileukin diftitox, dexrazoxane; docetaxel; doxorubicin; doxorubicin liposomal; Dromostanolone propionate; Elliott's B Solution; epirubicin; Epoetin alfa estramustine; etoposide phosphate; etoposide (VP-16); exemestane; Filgrastim; floxuridine (intraarterial); fludarabine; fluorouracil (5-FU); fulvestrant; gemtuzumab ozogamicin; gleevec (imatinib); goserelin acetate; hydroxyurea; Ibritumomab Tiuxetan; idarubicin; ifosfamide; imatinib mesylate; Interferon alfa-2a; Interferon alfa-2b; irinotecan; letrozole; leucovorin; levamisole; lomustine (CCNU); meclorethamine (nitrogen mustard); megestrol acetate; melphalan (L-PAM); mercaptopurine (6-MP); mesna; methotrexate; methoxsalen; mitomycin C; mitotane; mitoxantrone; nandrolone phenpropionate; Nofetumomab; LOddC; Oprelvekin; oxaliplatin; paclitaxel; pamidronate; pegademase; Pegaspargase; Pegfilg rastim; pentostatin; pipobroman; plicamycin; mithramycin; porfimer sodium; procarbazine; quinacrine; Rasburicase; Rituximab; Sargramostim; streptozocin; surafenib; talbuvidine (LDT); talc; tamoxifen; tarceva (erlotinib); temozolomide; teniposide (VM-26); testolactone; thioguanine (6-TG); thiotepa; topotecan; toremifene; Tositumomab; Trastuzumab; tretinoin (ATRA); Uracil Mustard; valrubicin; valtorcitabine (monoval LDC); vinblastine; vinorelbine; zoledronate; and mixtures thereof, among others.

Co-administration of one of the formulations of the invention with another anticancer agent will often result in a synergistic enhancement of the anticancer activity of the other anticancer agent, an unexpected result. One or more of the present formulations comprising an autophagy modulator may also be co-administered with another bioactive agent (e.g., antiviral agent, antihyperproliferative disease agent, agents which treat chronic inflammatory disease, among others as otherwise described herein).

The term "antiviral agent" refers to an agent which may be used in combination with autophagy modulators as otherwise described herein to treat viral infections, including HIV infections, HBV infections and/or HCV infections. Exemplary anti-HIV agents include, for example, nucleoside reverse transcriptase inhibitors (NRTI), non-nucleoside reverse transcriptase inhibitors (NNRTI), protease inhibitors, fusion inhibitors, among others, exemplary compounds of which may include, for example, 3TC (Lamivudine), AZT (Zidovudine), (−)-FTC, ddI (Didanosine), ddC (zalcitabine), abacavir (ABC), tenofovir (PMPA), D-D4FC (Reverset), D4T (Stavudine), Racivir, L-FddC, L-FD4C, NVP (Nevirapine), DLV (Delavirdine), EFV (Efavirenz), SQVM (Saquinavir mesylate), RTV (Ritonavir), IDV (Indinavir), SQV (Saquinavir), NFV (Nelfinavir), APV (Amprenavir), LPV (Lopinavir), fusion inhibitors such as T20, among others, fuseon and mixtures thereof, including anti-HIV compounds presently in clinical trials or in development. Exemplary anti-HBV agents include, for example, hepsera (adefovir dipivoxil), lamivudine, entecavir, telbivudine, tenofovir, emtricitabine, clevudine, valtoricitabine, amdoxovir, pradefovir, racivir, BAM 205, nitazoxanide, UT 231-B, Bay 41-4109, EHT899, zadaxin (thymosin alpha-1) and mixtures thereof, Anti-HCV agents include for example, interferon, pegylated intergeron, ribavirin, NM 283, VX-950 (telaprevir), SCH 50304, TMC435, VX-500, BX-813, SCH503034, R1626, ITMN-191 (R7227), R7128, PF-868554, TT033, CGH-759, GI 5005, MK-7009, SIRNA-034, MK-0608, A-837093, GS 9190, ACH-1095, GSK625433, TG4040 (MVA-HCV), A-831, F351, NS5A, NS4B, ANA598, A-689, GNI-104, IDX102, ADX184, GL59728, GL60667, PSI-7851, TLR9 Agonist, PHX1766, SP-30 and mixtures thereof.

The term "compound" is used herein to refer to any specific chemical compound disclosed herein.

In certain non-limiting embodiments, an increase or a decrease in a subject or test sample of the level of measured protein or gene expression or autophagic change as compared to a comparable level of measured protein or gene expression or autophagic change in a control subject or sample can be an increase or decrease in the magnitude of approximately ±5,000-10,000%, or approximately ±2,500-5,000%, or approximately ±1,000-2,500%, or approximately ±500-1,000%, or approximately ±250-500%, or approximately ±100-250%, or approximately ±50-100%, or approximately ±25-50%, or approximately ±10-25%, or approximately ±10-20%, or approximately ±10-15%, or approximately ±5-10%, or approximately ±1-5%, or approximately ±0.5-1%, or approximately ±0.1-0.5%, or approximately ±0.01-0.1%, or approximately ±0.001-0.01%, or approximately ±0.0001-0.001%.

The values obtained from controls are reference values representing a known health status and the values obtained from test samples or subjects are reference values representing a known disease status. The term "control," as used herein, can mean a sample of preferably the same source (e.g. blood, serum, tissue etc.) which is obtained from at least one healthy subject to be compared to the sample to be analyzed. In order to receive comparable results the control as well as the sample should be obtained, handled and treated in the same way. In certain examples, the number of healthy individuals used to obtain a control value may be at least one, preferably at least two, more preferably at least five, most preferably at least ten, in particular at least twenty. However, the values may also be obtained from at least one hundred, one thousand or ten thousand individuals.

The term "patient" or "subject" refers to an animal, such as a mammal, or a human, in need of treatment or therapy to which compounds according to the present invention are administered in order to treat a condition or disease state associated with autophagy.

The term "sample" encompasses a variety of sample types obtained from an organism and can be used in a diagnostic or monitoring assay. The term encompasses blood and/or plasma and other liquid samples of biological origin, solid tissue samples, such as a biopsy specimen or tissue cultures or cells derived therefrom and the progeny thereof. The term encompasses samples that have been manipulated in any way after their procurement, such as by treatment with reagents, solubilization, or enrichment for certain components. The term encompasses a clinical sample, and also includes cells in cell culture, cell supernatants, cell lysates, serum, plasma, biological fluids, and tissue samples.

The term "body fluid" refers to a biological sample of liquid from a mammal, e.g., from a human. Such fluids include aqueous fluids such as serum, plasma, lymph fluid, synovial fluid, follicular fluid, seminal fluid, amniotic fluid, milk, whole blood, urine, cerebrospinal fluid, saliva, sputum, tears, perspiration, mucus, tissue culture medium, tissue extracts, and cellular extracts. Particular bodily fluids that are interest in the context of the present invention include serum, plasma, and blood.

According to various embodiments, the compounds according to the present invention may be used for treatment or prevention purposes in the form of a pharmaceutical composition. This pharmaceutical composition may comprise one or more of compound, or active ingredient, as described herein.

The pharmaceutical composition may also comprise a pharmaceutically acceptable excipient, additive or inert carrier. The pharmaceutically acceptable excipient, additive or inert carrier may be in a form chosen from a solid, semi-solid, and liquid. The pharmaceutically acceptable excipient or additive may be chosen from a starch, crystalline cellulose, sodium starch glycolate, polyvinylpyrolidone, polyvinylpolypyrolidone, sodium acetate, magnesium stearate, sodium lauryl sulfate, sucrose, gelatin, silicic acid, polyethylene glycol, water, alcohol, propylene glycol, vegetable oil, corn oil, peanut oil, olive oil, surfactants, lubricants, disintegrating agents, preservative agents, flavoring agents, pigments, and other conventional additives. The pharmaceutical composition may be formulated by admixing the active with a pharmaceutically acceptable excipient or additive.

The pharmaceutical composition may be in a form chosen from sterile isotonic aqueous solutions, pills, drops, pastes, cream, spray (including aerosols), capsules, tablets, sugar coating tablets, granules, suppositories, liquid, lotion, suspension, emulsion, ointment, gel, and the like. Administration route may be chosen from subcutaneous, intravenous, intestinal, parenteral, oral, buccal, nasal, intramuscular, transcutaneous, transdermal, intranasal, intraperitoneal, and topical. The pharmaceutical compositions may be immediate release, sustained/controlled release, or a combination of immediate release and sustained/controlled release depending upon the compound(s) to be delivered, the compound(s), if any, to be coadministered, as well as the disease state and/or condition to be treated with the pharmaceutical composition. A pharmaceutical composition may be formulated with differing compartments or layers in order to facilitate effective administration of any variety consistent with good pharmaceutical practice.

The subject or patient may be chosen from, for example, a human, a mammal such as domesticated animal, or other animal. The subject may have one or more of the disease states, conditions or symptoms associated with autophagy as otherwise described herein.

The compounds according to the present invention may be administered in an effective amount to treat or reduce the likelihood of an autophagy-mediated disease and/or condition as well one or more symptoms associated with the disease state or condition. One of ordinary skill in the art would be readily able to determine an effective amount of active ingredient by taking into consideration several variables including, but not limited to, the animal subject, age, sex, weight, site of the disease state or condition in the patient, previous medical history, other medications, etc.

For example, the dose of an active ingredient which is useful in the treatment of an autophagy mediated disease state, condition and/or symptom for a human patient is that which is an effective amount and may range from as little as 100 µg or even less to at least about 500 mg or more, which may be administered in a manner consistent with the delivery of the drug and the disease state or condition to be treated. In the case of oral administration, active is generally administered from one to four times or more daily. Transdermal patches or other topical administration may administer drugs continuously, one or more times a day or less frequently than daily, depending upon the absorptivity of the active and delivery to the patient's skin. Of course, in certain instances where parenteral administration represents a favorable treatment option, intramuscular administration or slow IV drip may be used to administer the pharmaceutical composition. The amount of active ingredient which is administered to a human patient preferably ranges from about 0.05 mg/kg to about 10 mg/kg, about 0.1 mg/kg to about 7.5 mg/kg, about 0.25 mg/kg to about 6 mg/kg, about 1.25 to about 5.7 mg/kg.

The compound according to the present invention may be administered at the first signs of the onset of an autophagy mediated disease state, condition or symptom. For example, the compound may be administered for the purpose of lung or heart function and/or treating or reducing the likelihood of any one or more of the disease states or conditions which become manifest during an inflammation-associated metabolic disorder or tuberculosis or associated disease states or conditions, including pain, high blood pressure, renal failure, or lung failure. The dose of active ingredient may be administered at the first sign of relevant symptoms prior to diagnosis, in anticipation of the disease or disorder, or in anticipation of decreased bodily function or any one or more of the other symptoms or secondary disease states or conditions associated with an autophagy mediated disorder to condition.

These and other aspects of the invention are described further in the following illustrative examples.

EXAMPLES

Example 1

Preparation of 3-(4-methoxyphenyl)-1,5-bis(2-methoxyphenyl)-1,5-pentanedione (BPY-103), 3 ml p-methoxybenzaldehyde (24.7 mmoles), 6.8 milliliters (ml) 2-methoxyacetophenoe (49.4 mmoles), 20 ml of reagent alcohol (90% ethanol, 5% methanol, 5% isopropanol), and a stir bar was added to a 50 ml round-bottom flask. 3.3 g of KOH (85%) in 15 ml of water was then added to the flask, which caused the reaction mixture to become opaque within 5 minutes. The flask was then fitted with a septum and heated under nitrogen in a 105° C. sand bath for 12 hours. After this time, the crude product was precipitated in 200 ml of water before filtering and washing with methanol. The pure product was then recrystallized from methanol, yielding 2.34 grams (g) of 3-(4-methoxyphenyl)-1,5-bis(2-methoxyphenyl)-1,5-pentanedione. A further recrystallization from the mother liquor yielded a further 1.10 g of 3-(4-methoxyphenyl)-1,5-bis(2-methoxyphenyl)-1,5-pentanedione. The total yield was 3.44 g (33.3%)

$^1$H NMR (90 MHz, CDCl3): δ=7.55-6.85 (m, 12H, aromatics), 3.932 (s, 1H), 3.882 (s, 6H, peripheral methoxy groups), 3.788 (s, 3H, central methoxy groups), 3.412 (2H, $CH_2$), 3.332 (2H, $CH_2$). Melting range: 95-97° C.

Example 2

Preparation of 3-(4-allyloxyphenyl)-1,5-bis(2-methoxyphenyl)-1,5-pentanedione (BPY-101A)

0.93 g (4.89 mmoles) of BPY-101B (described in Example 2), 10 ml reagent alcohol (90% ethanol, 5% methanol, 5% isopropanol), a stir bar, and 1.6 ml 2-methoxyacetophenone was added to a 50 ml round-bottom flask. The flask was purged with $N_2$ for 5 min, and 0.67 g of 85% KOH in 10 ml of water was added, which caused immediate precipitation. More reagent alcohol was added until the precipitates were re-dissolved, giving a solution with a strong yellow color. The flask was then placed in a 105° C. sand bath for 19 hours, while the contents were stirred under a nitrogen atmosphere. After this time, the reaction mixture was precipitated into 300 ml of pH≅4 water, and the solids filtered and recrystallized from methanol. 1.08 g of the compound was recovered (49.7%)

$^1$H NMR (90 MHz, CDCl$_3$): δ=7.618-6.811 (m, 12H, aromatics), 6.042 (m, 1H, allyl CH$_2$—C$\underline{H}$=CH$_2$), 5.564 (dd, 1H, allyl CH$_2$—CH=C$\underline{H}_2$) 5.339 (dd, 1H, allyl CH$_2$—CH=C$\underline{H}_2$) 3.972 (1 h, partially obscured), 3.926 (s, 6H, methoxy), 3.461 (2H, C$\underline{H}_2$), 3.382 (2H, C$\underline{H}_2$). Melting range: 86-88° C.

Example 3

Preparation of 3-(4-hydroxyphenyl)-1,5-bis(2-methoxyphenyl)-1,5-pentanedione (BPY-101)

1.09 g BPY-101A (described in Example 3), 15 ml methanol, and 0.46 g sodium tert-butoxide was added to a 50 ml round bottomed flask. The mixture was sparged with N$_2$ and stirred for 15 minutes. After this time, 0.46 g tetrakis (triphenylphosphine)palladium(0) was added to the reaction mixture and stirred under N$_2$ with occasional heating to re-dissolve particulates. After 1 hour, only one spot on the baseline remained in TLC (CHCl$_3$). The reaction mixture was added to 100 ml pH≅12 water and washed with 2×100 CHCl$_3$. The water phase was then acidified (pH≅4) with HCl, and extracted with 3×300 ml CHCl$_3$. The organic phase was then dried over Na$_2$SO$_4$ and reduced in vaccuo leaving an orange solid.

$^1$H NMR (90 MHz, CDCl$_3$): δ=7.574-6.645 (m, 12H, aromatics), 3.897 (s, 6H, methoxy), 3.429 (2H, C$\underline{H}_2$), 3.351 (2H, C$\underline{H}_2$). Note: The single proton peak could not be definitely assigned and is most likely overlapped by the methoxy peaks.

Example 4

Preparation of 2,6-di(2-methoxyphenyl)-4-(4-methoxyphenyl) pyridine (BPY-104)

Into a 50 ml round-bottomed flask was added 0.52 g of 3-(4-methoxyphenyl)-1,5-bis(2-methoxyphenyl)-1,5-pentanedione (BPY-103), 20 ml of glacial acetic acid, a stir bar and 3.1 g ammonium acetate. The flask was fitted with a reflux condenser and the solution was refluxed while stirring for 4 h. The flask was then removed from heat and the crude product was precipitated into 300 ml of water. The pure product was obtained by recrystallization from a mixture of chloroform and methanol. Formation of the product was confirmed by the disappearance of the CH$_2$ peaks at 3.412 ppm and 3.332 ppm in the NMR spectrum, and also by the dramatic increase in melting range. $^1$H NMR (90 MHz, CDCl$_3$): δ=7.95-6.75 m, 14H, aromatic), 3.9-3.7 (9H, methoxy). Melting range: 188-190° C.

Although the present invention has been described in considerable detail with reference to certain preferred embodiments, other embodiments are possible. The steps disclosed for the present methods, for example, are not intended to be limiting nor are they intended to indicate that each step is necessarily essential to the method, but instead are exemplary steps only. Therefore, the scope of the appended claims should not be limited to the description of preferred embodiments contained in this disclosure. All references cited herein are incorporated by reference in their entirety.

FEATURES OF THE INVENTION

1. A compound having the following structural formula:

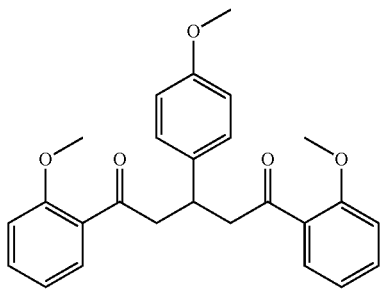 [SMILES: COc1ccc(C(CC(=O)c2ccccc2OC)CC(=O)c2ccccc2OC)cc1]

2. A compound having the following structural formula:

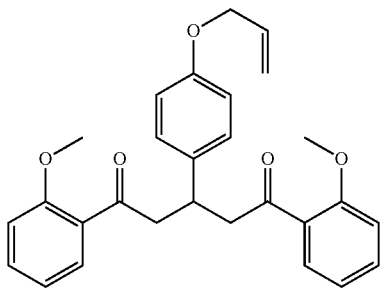 [SMILES: C=CCOc1ccc(C(CC(=O)c2ccccc2OC)CC(=O)c2ccccc2OC)cc1]

3. A compound having the following structural formula:

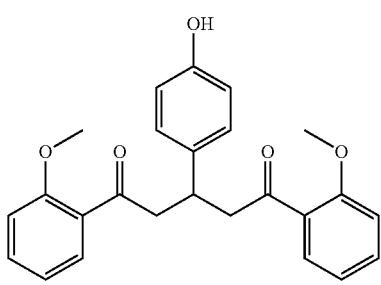 [SMILES: COc1ccccc1C(=O)CC(CC(=O)c1ccccc1OC)c1ccc(O)cc1]

4. A compound having the following structural formula:

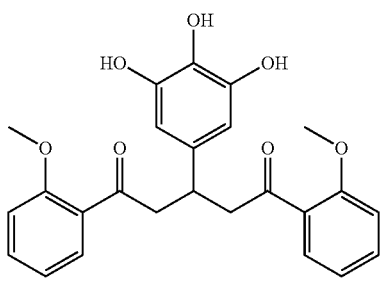 [SMILES: COc1ccccc1C(=O)CC(CC(=O)c1ccccc1OC)c1cc(O)c(O)c(O)c1]

5. A compound having the following structural formula:

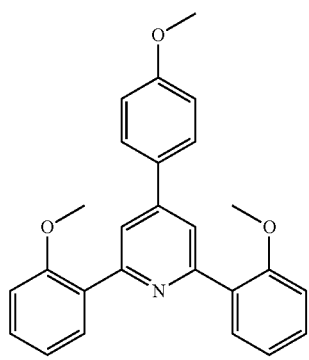 [SMILES: COc1ccc(-c2cc(-c3ccccc3OC)nc(-c3ccccc3OC)c2)cc1]

6. A compound having the following structural formula:

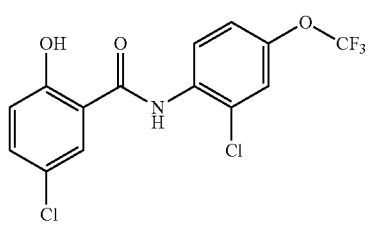 [SMILES: O=C(Nc1ccc(OC(F)(F)F)cc1Cl)c1cc(Cl)ccc1O]

7. A compound having the following structural formula:

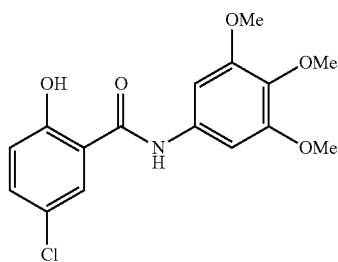 [SMILES: COc1cc(NC(=O)c2cc(Cl)ccc2O)cc(OC)c1OC]

8. A compound having the following structural formula:

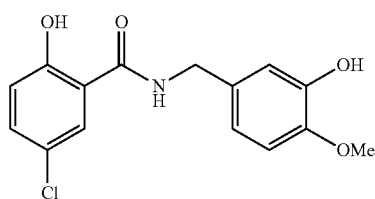 [SMILES: COc1ccc(CNC(=O)c2cc(Cl)ccc2O)cc1O]

9. A compound having the following structural formula:

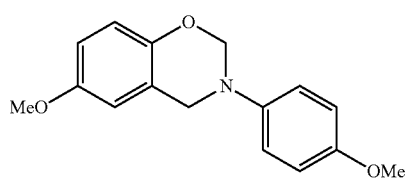

10. A compound having the following structural formula:

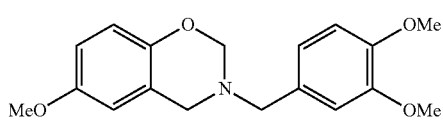 [SMILES: COc1ccc2c(c1)CN(Cc1ccc(OC)c(OC)c1)CO2]

11. A compound having the following structural formula:

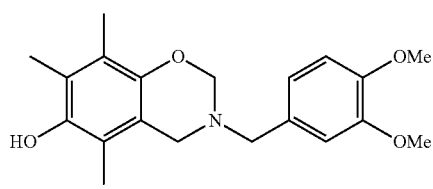 [SMILES: COc1ccc(CN2COc3c(C)c(C)c(O)c(C)c3C2)cc1OC]

12. A compound having the following structural formula:

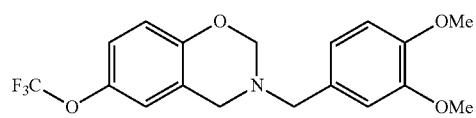 [SMILES: COc1ccc(CN2COc3ccc(OC(F)(F)F)cc3C2)cc1OC]

13. A compound having the following structural formula:

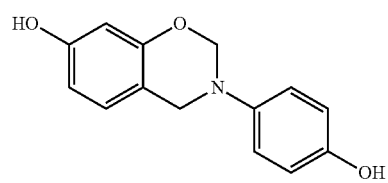 [SMILES: Oc1ccc(N2COc3cc(O)ccc3C2)cc1]

14. A compound having the following structural formula:

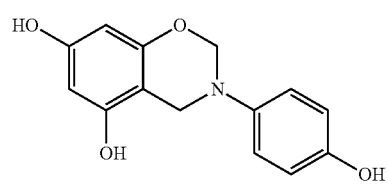 [SMILES: Oc1ccc(N2COc3cc(O)cc(O)c3C2)cc1]

15. A compound having the following structural formula:

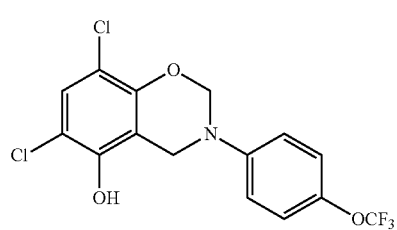 [SMILES: Oc1c(Cl)cc(Cl)c2c1CN(c1ccc(OC(F)(F)F)cc1)CO2]

16. A compound having the following structural formula:

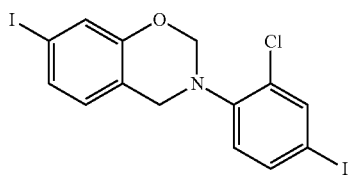 [SMILES: Clc1cc(I)ccc1N1COc2cc(I)ccc2C1]

17. A compound having the following structural formula:

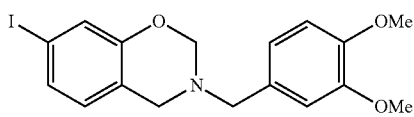 [SMILES: COc1ccc(CN2COc3cc(I)ccc3C2)cc1OC]

18. A compound having the following structural formula:

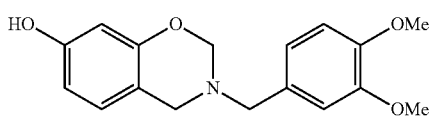

19. A compound having the following structural formula:

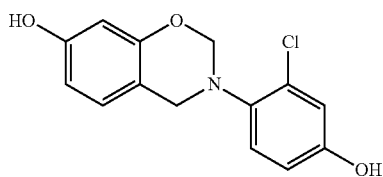 [SMILES: Oc1ccc(N2COc3cc(O)ccc3C2)c(Cl)c1]

20. A compound having the following structural formula:

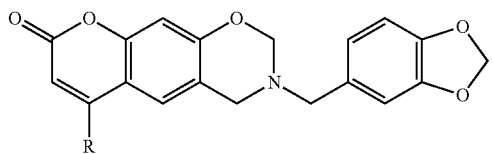

21. A method of using the compound of any of features 1-20 to treat an autophagy-mediated disease state or condition.

22. The method of feature 21, wherein the autophagy-mediated disease state or condition is cancer, lysosomal storage diseases, Alzheimer's disease, Parkinson's disease and other ataxias such as Huntington's disease; a chronic inflammatory disease such as Crohn's disease, diabetes I, diabetes II, metabolic syndrome, an inflammation-associated metabolic disorder, liver disease, renal disease, cardiovascular disease, muscle degeneration and atrophy, frailty in aging, spinal cord injury, infectious disease, chronic pain, depression related syndromes, and developmental disease.

23. The method according to feature 22 wherein the cancer is stomach, colon, rectal, liver, pancreatic, lung, breast, cervix uteri, corpus uteri, ovary, prostate, testis, bladder, renal, brain/CNS, head and neck, throat, Hodgkin's disease, non-Hodgkin's lymphoma, multiple myeloma, leukemia, melanoma, non-melanoma skin cancer, acute lymphocytic leukemia, acute myelogenous leukemia, Ewing's sarcoma, small cell lung cancer, choriocarcinoma, rhabdomyosarcoma, Wilms' tumor, neuroblastoma, hairy cell leukemia, mouth/pharynx, esophagus, larynx, kidney cancer or lymphoma.

24. The method according to feature 22 wherein the chronic inflammatory disease is inflammatory bowel disease, rheumatoid arthritis, lupus, multiple sclerosis, chronic obstructive pulmonary disease/COPD, pulmonary fibrosis, cystic fibrosis or Sjogren's disease.

25. The method according to feature 22 wherein the cardiovascular disease is ischemia, stroke, pressure overload, complications during reperfusion and arteriosclerosis.

26. The method according to feature 22 wherein the infectious disease is a viral infection or a secondary condition of the viral infection.

27. The method according to feature 26 wherein the viral infection is HIV (I and or II) and said secondary condition is AIDS, hepatitis B virus (HBV) or hepatitis C virus, influenza virus and herpes virus.

28. The method according to feature 22 wherein said lysosomal storage disease is activator deficiency/GM2 gangliosidosis, alpha-mannosidosis, aspartylglucoaminuria, cholesteryl ester storage disease, chronic hexosaminidase A deficiency, cystinosis, Danon disease, Fabry disease, Farber disease, fucosidosis, galactosialidosis, Gaucher Disease (Types I, II and III), GM1 Ganliosidosis, including infantile, late infantile/juvenile and adult/chronic), Hunter syndrome (MPS II), I-Cell disease/Mucolipidosis II, Infantile Free Sialic Acid Storage Disease (ISSD), Juvenile Hexosaminidase A Deficiency, Krabbe disease, Lysosomal acid lipase deficiency, Metachromatic Leukodystrophy, Hurler syndrome, Scheie syndrome, Hurler-Scheie syndrome, Sanfilippo syndrome, Morquio Type A and B, Maroteaux-Lamy, Sly syndrome, mucolipidosis, multiple sulfate deficiency, Niemann-Pick disease, Neuronal ceroid lipofuscinoses, CLN6 disease, Jansky-Bielschowsky disease, Pompe disease, pycnodysostosis, Sandhoff disease, Schindler disease, Tay-Sachs or Wolman disease.

29. A pharmaceutical composition comprising:
 (a) the compound of features 1-20 in an effective amount; and optionally
 (b) a pharmaceutically-acceptable carrier, additive and/or excipient, and further optionally;
 (c) at least one additional bioactive agent.
 or a secondary condition of the viral infection.

30. The composition according to feature 29 wherein the additional autophagy modulator is selected from the group consisting of benzethonium, niclosamide, monensin, bromperidol, levobunolol, dehydroisoandosterone 3-acetate, sertraline, tamoxifen, reserpine, hexachlorophene, dipyridamole, harmaline, prazosin, lidoflazine, thiethylperazine, dextromethorphan, desipramine, mebendazole, canrenone, chlorprothixene, maprotiline, homochlorcyclizine, loperamide, nicardipine, dexfenfluramine, nilvadipine, dosulepin, biperiden, denatonium, etomidate, toremifene, tomoxetine, clorgyline, zotepine, beta-escin, tridihexethyl, ceftazidime, methoxy-6-harmalan, melengestrol, albendazole, rimantadine, chlorpromazine, pergolide, cloperastine, prednicarbate, haloperidol, clotrimazole, nitrofural, iopanoic acid, naftopidil, methimazole, trimeprazine, ethoxyquin, clocortolone, doxycycline, pirlindole mesylate, doxazosin, deptropine, nocodazole, scopolamine, oxybenzone, halcinonide, oxybutynin, miconazole, clomipramine, cyproheptadine, doxepin, dyclonine, salbutamol, flavoxate, amoxapine, fenofibrate, pimethixene, pharmaceutically acceptable salts thereof and mixtures thereof.

16. The composition according to feature 29 wherein the additional bioactive agent is an antibiotic or an antiviral agent.

17. The composition according to feature 29 wherein the bioactive agent includes an anticancer agent.

What is claimed is:

1. A compound of the formula:

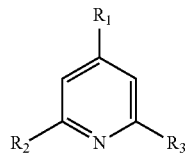

wherein $R^1$ represents 4-methoxyphenyl;
wherein $R^2$ represents 2-methoxyphenyl; and
wherein $R^3$ represents 3-methoxyphenyl.

2. The compound of claim 1, wherein the compound is 2-(2-methoxyphenyl)-6-(3-methoxyphenyl)-4-(4-methoxyphenyl) pyridine.

3. The compound of claim 2, wherein the compound is used to treat an autophagy-mediated disease state or condition.

4. The compound of claim 3, wherein the autophagy-mediated disease state or condition that the compound is used to treat is cancer, lysosomal storage diseases, Alzheimer's disease, Parkinson's disease and other ataxias such as Huntington's disease; a chronic inflammatory disease such as Crohn's disease, diabetes I, diabetes II, metabolic syndrome, an inflammation-associated metabolic disorder, liver disease, renal disease, cardiovascular disease, muscle degeneration and atrophy, frailty in aging, spinal cord injury, infectious disease, chronic pain, depression related syndromes, and developmental disease.

5. The compound of claim 2, wherein a pharmaceutical composition comprises an effective amount of the compound of claim 2.

6. The compound of claim 5, further comprising at least one additional bioactive agent or a secondary condition of the viral infection.

7. The compound of claim 5 wherein the composition further comprises an autophagy modulator selected from the group comprising benzethonium, niclosamide, monensin, bromperidol, levobunolol, dehydroisoandosterone 3-acetate, sertraline, tamoxifen, reserpine, hexachlorophene, dipyridamole, harmaline, prazosin, lidoflazine, thiethylperazine, dextromethorphan, desipramine, mebendazole, canrenone, chlorprothixene, maprotiline, homochlorcyclizine, loperamide, nicardipine, dexfenfluramine, nilvadipine, dosulepin, biperiden, denatonium, etomidate, toremifene, tomoxetine, clorgyline, zotepine, beta-escin, tridihexethyl, ceftazidime, methoxy-6-harmalan, melengestrol, albendazole, rimantadine, chlorpromazine, pergolide, cloperastine, prednicarbate, haloperidol, clotrimazole, nitrofural, iopanoic acid, naftopidil, methimazole, trimeprazine, ethoxyquin, clocortolone, doxycycline, pirlindole mesylate, doxazosin, deptropine, nocodazole, scopolamine, oxybenzone, halcinonide, oxybutynin, miconazole, clomipramine, cyproheptadine, doxepin, dyclonine, salbutamol, flavoxate, amoxapine, fenofibrate, pimethixene, pharmaceutically acceptable salts thereof and mixtures thereof.

8. The compound of claim 6, wherein the additional bioactive agent is an antibiotic, an antiviral agent, or an anticancer agent.

9. A compound of the formula:

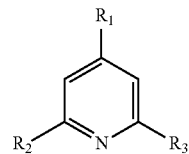

wherein $R^1$ is selected from the group consisting of 2-bromo-4,5-methylenedioxyphenyl, 3-methoxyphenyl, 4-methoxyphenyl, 4-hydroxyphenyl,
and $R_2$ and $R_3$ are equivalent, and are selected from the group consisting of 3,4-methylenedioxyphenyl, 3-methoxyphenyl, or 2,4-dimethoxyphenyl.

10. The compound of claim 9, wherein the compound is selected from the group consisting of:
2,6-di(3,4-methylenedioxyphenyl)-4-(4-methoxyphenyl) pyridine,
2,6-di(3,4-methylenedioxyphenyl)-4-(2-bromo-4,5-methylenedioxyphenyl)pyridine,
2,6-di(2-methoxyphenyl)-4-(3,4-dimethoxyphenyl) pyridine, and
2,6-di(3-methoxyphenyl)-4-(4-methoxyphenyl) pyridine.

11. The compound of claim 10, wherein the compound is used to treat an autophagy-mediated disease state or condition.

12. The compound of claim 11, wherein the autophagy-mediated disease state or condition that the compound is used to treat is cancer, lysosomal storage diseases, Alzheimer's disease, Parkinson's disease and other ataxias such as Huntington's disease: a chronic inflammatory disease such as Crohn's disease, diabetes I, diabetes II, metabolic syndrome, an inflammation-associated metabolic disorder, liver disease, renal disease, cardiovascular disease, muscle degeneration and atrophy, frailty in aging, spinal cord injury, infectious disease, chronic pain, depression related syndromes, and developmental disease.

13. The compound of claim 10, wherein a pharmaceutical composition comprises an effective amount of the compound of claim 10.

14. The compound of claim 13, further comprising at least one additional bioactive agent or a secondary condition of the viral infection.

15. The compound of claim 13, further comprising an autophagy modulator selected from the group comprising benzethonium, niclosamide, monensin, bromperidol, levobunolol, dehydroisoandosterone 3-acetate, sertraline, tamoxifen, reserpine, hexachlorophene, dipyridamole, harmaline, prazosin, lidoflazine, thiethylperazine, dextromethorphan, desipramine, mebendazole, canrenone, chlorprothixene, maprotiline, homochlorcyclizine, loperamide, nicardipine, dexfenfluramine, nilvadipine, dosulepin, biperiden, denatonium, etomidate, toremifene, tomoxetine, clorgyline, zotepine, beta-escin, tridihexethyl, ceftazidime, methoxy-6-harmalan, melengestrol, albendazole, rimantadine, chlorpromazine, pergolide, cloperastine, prednicarbate, haloperidol, clotrimazole, nitrofural, iopanoic acid, naftopidil, methimazole, trimeprazine, ethoxyquin, clocortolone, doxycycline, pirlindole mesylate, doxazosin, deptropine, nocodazole, scopolamine, oxybenzone, halcinonide, oxybutynin, miconazole, clomipramine, cyproheptadine, doxepin, dyclonine, salbutamol, flavoxate, amoxapine, fenofibrate, pimethixene, pharmaceutically acceptable salts thereof and mixtures thereof.

16. The compound of claim 15, wherein the additional bioactive agent is an antibiotic, an antiviral agent, or an anticancer agent.

17. A compound of the formula:

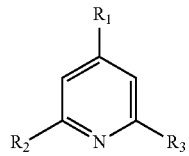

wherein $R_1$ is selected from 2-bromo-4,5-methylenedioxyphenyl, 3-methoxyphenyl, 4-acetomidylphenyl, cyanophenyl, carboxyphenyl or 3,4-methylendioxyphenyl, and wherein $R_2$ and $R_3$ are equivalent, and are selected from 2-methoxyphenyl, 3-methoxyphenyl, or 4-methoxyphenyl.

18. The compound of claim 17, wherein the compound is selected from the group consisting of:
2,6-di(2-methoxyphenyl)-4-(2-bromo-4,5-methylenedioxyphenyl) pyridine,
2,6-di(2-methoxyphenyl)-4-(3-methoxyphenyl) pyridine,
2,6-di(2-methoxyphenyl)-4-(4-acetomidophenyl) pyridine,
2,6-di(2-methoxyphenyl)-4-(4-cyanophenyl) pyridine,
2,6-di(2-methoxyphenyl)-4-(3-cyanophenyl) pyridine,
2,6-di(2-methoxyphenyl)-4-(4-carboxyphenyl) pyridine, and
2,6-di(2,4-dimethoxyphenyl)-4-(4-hydroxyphenyl) pyridine.

19. The compound of claim 18, wherein the compound is used to treat an autophagy-mediated disease state or condition.

20. The compound of claim 19, wherein the autophagy-mediated disease state or condition that the compound is used to treat is cancer, lysosomal storage diseases, Alzheimer's disease, Parkinson's disease and other ataxias such as Huntington's disease: a chronic inflammatory disease such as Crohn's disease, diabetes I, diabetes II, metabolic syndrome, an inflammation-associated metabolic disorder, liver disease, renal disease, cardiovascular disease, muscle degeneration and atrophy, frailty in aging, spinal cord injury, infectious disease, chronic pain, depression related syndromes, and developmental disease.

21. The compound of claim 18, wherein a pharmaceutical composition comprises an effective amount of the compound of claim 18.

22. The compound of claim 21, further comprising at least one additional bioactive agent or a secondary condition of the viral infection.

23. The compound of claim 21, further comprising an autophagy modulator selected from the group comprising benzethonium, niclosamide, monensin, bromperidol, levobunolol, dehydroisoandosterone 3-acetate, sertraline, tamoxifen, reserpine, hexachlorophene, dipyridamole, harmaline, prazosin, lidoflazine, thiethylperazine, dextromethorphan, desipramine, mebendazole, canrenone, chlorprothixene, maprotiline, homochlorcyclizine, loperamide, nicardipine, dexfenfluramine, nilvadipine, dosulepin, biperiden, denatonium, etomidate, toremifene, tomoxetine, clorgyline, zotepine, beta-escin, tridihexethyl, ceftazidime, methoxy-6-harmalan, melengestrol, albendazole, rimantadine, chlorpromazine, pergolide, cloperastine, prednicarbate, haloperidol, clotrimazole, nitrofural, iopanoic acid, naftopidil, methimazole, trimeprazine, ethoxyquin, clocortolone, doxycycline, pirlindole mesylate, doxazosin, deptropine, nocodazole, scopolamine, oxybenzone, halcinonide, oxybutynin, miconazole, clomipramine, cyproheptadine, doxepin, dyclonine, salbutamol, flavoxate, amoxapine, fenofibrate, pimethixene, pharmaceutically acceptable salts thereof and mixtures thereof.

24. The compound of claim 22, wherein the additional bioactive agent is an antibiotic, an antiviral agent, or an anticancer agent.

25. A compound of the formula:

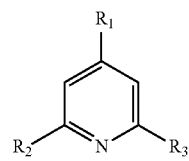

wherein $R_1$ is selected from the group consisting of 2-bromo-4,5-methylenedioxyphenyl, 3-methoxyphenyl, 4-acetomidylphenyl, cyanophenyl, carboxyphenyl and 3,4-methylendioxyphenyl, and wherein $R_2$ is selected from the group consisting of 2-methoxyphenyl, 3-methoxyphenyl, 4-methoxyphenyl, dimethoxyphenyl, and methylenedioxyphenyl, and wherein $R_3$ is selected from the group consisting of 2-methoxyphenyl, 3-methoxyphenyl, 4-methoxyphenyl, dimethoxyphenyl, and methylenedioxyphenyl.

26. The compound of claim 25, wherein the compound is selected from the group consisting of:
2-(3-methoxyphenyl)-6-(4-methoxyphenyl)-4-(4-methoxyphenyl) pyridine, and
2-(3,4-methylenedioxy)-6-(3-methoxyphenyl)-4-(4-methoxyphenyl) pyridine.

27. The compound of claim 26, wherein the compound is used to treat an autophagy-mediated disease state or condition.

28. The compound of claim 27, wherein the autophagy-mediated disease state or condition that the compound is used to treat is cancer, lysosomal storage diseases, Alzheimer's disease, Parkinson's disease and other ataxias such as Huntington's disease; a chronic inflammatory disease such as Crohn's disease, diabetes I, diabetes II, metabolic syndrome, an inflammation-associated metabolic disorder, liver disease, renal disease, cardiovascular disease, muscle degeneration and atrophy, frailty in aging, spinal cord injury, infectious disease, chronic pain, depression related syndromes, and developmental disease.

29. The compound of claim 26, wherein a pharmaceutical composition comprises an effective amount of the compound of claim 26.

30. The compound of claim 26, further comprising at least one additional bioactive agent or a secondary condition of the viral infection.

31. The compound of claim 26, further comprising an autophagy modulator selected from the group comprising benzethonium, niclosamide, monensin, bromperidol, levobunolol, dehydroisoandosterone 3-acetate, sertraline, tamoxifen, reserpine, hexachlorophene, dipyridamole, harmaline, prazosin, lidoflazine, thiethylperazine, dextromethorphan, desipramine, mebendazole, canrenone, chlorprothixene, maprotiline, homochlorcyclizine, loperamide, nicardipine, dexfenfluramine, nilvadipine, dosulepin, biperiden, denatonium, etomidate, toremifene, tomoxetine, clorgyline, zotepine, beta-escin, tridihexethyl, ceftazidime, methoxy-6-harmalan, melengestrol, albendazole, rimantadine, chlorpromazine, pergolide, cloperastine, prednicarbate, haloperidol, clotrimazole, nitrofural, iopanoic acid, naftopidil, methimazole, trimeprazine, ethoxyquin, clocortolone, doxycycline, pirlindole mesylate, doxazosin, deptropine, nocodazole, scopolamine, oxybenzone, halcinonide, oxybutynin, miconazole, clomipramine, cyproheptadine, doxepin, dyclonine, salbutamol, flavoxate, amoxapine, fenofibrate, pimethixene, pharmaceutically acceptable salts thereof and mixtures thereof.

32. The compound of claim 30, wherein the additional bioactive agent is an antibiotic, an antiviral agent, or an anticancer agent.

* * * * *